US012175387B2

(12) United States Patent
Bax et al.

(10) Patent No.: US 12,175,387 B2
(45) Date of Patent: Dec. 24, 2024

(54) CONTENT ITEM SELECTION FOR GOAL ACHIEVEMENT

(71) Applicant: Oath Inc., New York, NY (US)

(72) Inventors: Eric Theodore Bax, Sierra Madre, CA (US); Kimberly Williams, Burbank, CA (US); Lisa Giaffo, Pasadena, CA (US); Nikki Mia Williams, Gardena, CA (US); John Donald, Los Angeles, CA (US); Melissa Susan Gerber, Los Angeles, CA (US); Tanisha Sharma, Los Angeles, CA (US)

(73) Assignee: Yahoo Assets LLC, New York, NY (US)

( * ) Notice: Subject to any disclaimer, the term of this patent is extended or adjusted under 35 U.S.C. 154(b) by 1229 days.

(21) Appl. No.: 16/716,537

(22) Filed: Dec. 17, 2019

(65) Prior Publication Data

US 2021/0182700 A1 Jun. 17, 2021

(51) Int. Cl.
*G06N 5/00* (2023.01)
*G06N 5/046* (2023.01)
*G06N 20/00* (2019.01)
*G06Q 30/00* (2023.01)
*G06Q 30/0204* (2023.01)
*G06Q 50/00* (2024.01)
*G06Q 50/20* (2012.01)
*G16H 20/00* (2018.01)
*G16H 20/60* (2018.01)

(52) U.S. Cl.
CPC .............. *G06N 5/046* (2013.01); *G06N 20/00* (2019.01); *G06Q 30/0204* (2013.01); *G06Q 50/01* (2013.01); *G06Q 50/20* (2013.01); *G16H 20/60* (2018.01)

(58) Field of Classification Search
CPC ......... G06Q 10/00; G06Q 30/00; G06Q 50/00
USPC ......................................................... 705/7.33
See application file for complete search history.

(56) References Cited

U.S. PATENT DOCUMENTS

| 7,330,822 B1* | 2/2008 | Robson .......... G06Q 10/063118 705/7.17 |
| 11,301,764 B1* | 4/2022 | Wendel ................ G06Q 10/025 |
| 2005/0192831 A1* | 9/2005 | Ellison ............. G06Q 10/06398 705/345 |
| 2007/0162907 A1* | 7/2007 | Herlocker .............. G06Q 10/10 718/100 |
| 2018/0260748 A1* | 9/2018 | Olsen ..................... G06Q 10/10 |
| 2019/0012167 A1* | 1/2019 | Boss ...................... G06Q 50/01 |
| 2019/0122158 A1* | 4/2019 | Ukai ................ G06Q 10/06393 |
| 2019/0122162 A1* | 4/2019 | Abhinav ........ G06Q 10/063118 |

(Continued)

*Primary Examiner* — Mustafa Iqbal
(74) *Attorney, Agent, or Firm* — Cooper Legal Group LLC

(57) ABSTRACT

One or more computing devices, systems, and/or methods for content item selection for goal achievement are provided herein. A goal of a user is identified. A model is utilized to evaluate the goal, user information, and a set of content items to generate predictions for the content items of how likely each content item will be a causation factor of the user making progress towards the goal in response to the user being provided with each content item. A target content item is selected from the set of content items based upon the target content item having a predicted likelihood of being the causation factor above a threshold. The target content item is provided through a registered media channel accessible through a device of the user.

20 Claims, 11 Drawing Sheets

(56) References Cited

U.S. PATENT DOCUMENTS

2021/0103840 A1\* 4/2021 Kwong .................. G06N 20/00
2021/0224720 A1\* 7/2021 Makino .......... G06Q 10/063116

\* cited by examiner

CONTENT ITEM SELECTION FOR GOAL ACHIEVEMENT

BACKGROUND

A content recommendation component selects content items to provide to users based upon an objective. The content items may correspond to images, text, recommendations of activities or products, videos, links to websites or services, etc. The content items may be provided through email, a social network feed, a user interface, etc. In an example, the content recommendation component selects a content item to provide to a user based upon an objective corresponding to maximizing a probability that the user will experience the content item (e.g., a likelihood that the user will watch a video within a social media feed in order keep the user engaged with the social media feed).

In another example, the content recommendation component selects a content item to provide to a user based upon an objective corresponding to maximizing revenue. For example, the objective is to maximize revenue for an owner of a media service/system (e.g., a social media service, a website or application through which content items can be displayed, an email service through which users view emails, a video streaming service, a music streaming service, etc.). The revenue may be maximized through a combination of sales or rental of items to users, paid subscriptions, and/or advertising.

Unfortunately, the objectives used by the content recommendation component are not tailored to help and benefit the user. Instead, the objectives are profit driven for media services, such as where content items are selected for a user in order to keep the user engaged with a service longer so that more revenue generating opportunities (e.g., showing an advertisement, offering a service or item for sale, etc.) will be provided to the user.

SUMMARY

In accordance with the present disclosure, one or more computing devices and/or methods for content item selection for goal achievement are provided. A model may be trained to identify content items to provide to users based upon an objective corresponding to inspiring and/or motivating the users to work towards achieving their goals. In an embodiment, a goal may comprise a health goal. The health goal may correspond to a wide variety of health related goals, such as achieving or maintaining a healthy weight, blood pressure level, blood sugar level, or exercise routine, taking medicine as prescribed, monitoring health on a prescribed schedule, establishing or maintaining healthy eating habits, etc. In an embodiment, a goal may comprise a financial goal. The financial goal may correspond to a wide variety of financial related goals, such as saving for retirement, buying a home, remodeling a home, starting a business, investing, finding a new or better job, advancing in a current job, etc.

In an embodiment, a goal may comprise an education goal. The education goal may correspond to a wide variety of educational related goals, such as enrolling in or completing an online course or another course of study, obtaining acceptance to a college or graduate school, improving grades in school, learning a skill, learning a language, etc. In an embodiment, the goal may comprise a relationship goal. The relationship goal may correspond to a wide variety of relationship related goals, such as dating, marriage, maintaining a healthy marriage, finding new friends, maintaining healthy friendships, developing or maintaining healthy relationships with immediate or extended family, etc. In an embodiment, a goal may comprise a lifestyle goal. The lifestyle goal may corresponding to a wide variety of lifestyle related goals, such as embracing a new style in fashion, refining an old style in fashion, taking an enjoyable vacation, establishing or maintaining habits that are good for the environment, getting involved in a cause, becoming a sports fan, adopting a pet, improving athletic performance, etc.

In an embodiment, goals of users may be explicitly defined by the users. For example, a user may specify a goal to gain 5 pounds of muscle mass over a summer break from school. In an embodiment, such goals may be inferred from various signals, such as from email messages, text messages, social network posts, email receipts, bank statements, calendar entries, website browsing history, images viewed through an image sharing service, etc. For example, the user may view images about Germany, and then write a blog about wanting to learn the German language. The images and blog may be evaluated to infer that the user has a goal to learn the German language.

The model may be trained to select content items that will help motivate particular users to achieve certain goals. The model may be trained by performing statistical filtering on a set of content items to identify content items that correlate to goal progress for groups of users. For example, a group of 25 year old males living in Florida may have a tendency to gain muscle mass after watching rugby videos (e.g., after rugby videos are shown to these types of users, the users, personal trainers, and/or other data sources may provide muscle mass tracking data over time to a content recommendation component configured to train and utilize the model for selecting content items to provide to users). Because mere statistical filtering may be based upon correlation (e.g., user that watches a rugby video subsequently gained muscle mass), which is not always causation (e.g., did viewing a rugby video cause a user to perform an activity to gain muscle mass), causality testing (e.g., A/B testing) is performed to further train the model based upon causation. The causality testing takes into account whether users made progress towards a goal when shown a content item and whether users made progress towards the goal when not shown the content item. If many users still made progress towards the goal when not shown the content item, then there may be less causality of the content item causing users to make progress towards the goal.

Once trained, the model may be utilized to select a content item to provide to a user in order to motivate the user to make progress towards a goal. In an example, the goal of the user may be identified, such as either explicitly specified by the user or inferred based upon various signals. In an embodiment, a time limit may be imposed upon the goal, such as where the user wants to learn a language by the end of summer before school starts back when the user has little time or desire to continue working on learning the language. In an embodiment, the user may be clustered into a cluster of other similar users with similar goals. In this way, historical data of users within the cluster (e.g., information relating to what content items motivated users within the cluster to make progress towards the goal of learning the German language) is aggregated as an input into the model for selecting the content item to provide to the user.

The model is executed to evaluate the goal of the user, user information (e.g., age, gender, work location, home location, media type preference such as a particular social network, application, website, etc.), the aggregated historical data of similar users, and/or a set of content items to generate predictions for the content items of how likely each content item will be a causation factor of the user making progress towards the goal in response to the user being provided with each content item. In an embodiment, the model comprises a function. The function has an input of an item input (e.g., a content item), a user input (e.g., user information), and a goal input (e.g., the goal to learn the German language by the end of summer). Based upon the input, the function outputs an increased probability that the user will make progress towards the goal if provided with the content item. The output corresponds to a difference between a probability that the user will make progress towards the goal if provided with the content item and a probability that the user will make progress towards the goal if the user is not provided with the content item. In this way, each content item is assigned an output of how likely the content item is a causation factor (e.g., an increase in a probability that the user will make progress towards the goal if provided with a content item), which can be used to rank the content items. In an embodiment, one or more additional systems may be used to rank the content items. Such additional systems may utilize a different objective than the objective to motivate the user to make progress towards the goal. For example, a system with an objective to maximize a probability that the user will experience the item or an objective to maximize revenue may also be used to rank the content items.

A target content item is selected from the set of content items based upon the target content item having a predicted likelihood of being the causation factor above a threshold. For example, the target content item may be selected as a content item with a highest likelihood of being the causation factor (e.g., a largest increase in a probability that the user will make progress towards the goal if provided with the target content item). In this way, the target content item is provided to the user, such as through an application, a website, a social media feed, an image sharing service, an email, a message, a push notification, etc.

Progress of the user towards the goal may be monitored through various goal measurement feedback channels, such as user input, weight measurement from a scale, email content (e.g., the user emailing a friend about studying the German language the other day), calendar content (e.g., the user creating a calendar entry to study the German language), bank statements, receipts (e.g., the user purchasing a German language instructional video), information input by a third party such as a parent or doctor, activities performed by the user and tracked by a smart device, location information of the user, and/or a wide variety of information that can be obtained and evaluated to see if the user took action towards the goal. The goal progress data may be used to further train the model and to further select content items to provide to the user for making further progress towards the goal. The goal progress data may be used to subsequently select content items to show to the user (e.g., if the user made progress after being shown a certain type of video, then other similar videos may be shown to the user; if the user did not make progress after viewing an image having a particular theme, then different types of content than the image and/or different themes than the theme may be selected; etc.).

In an embodiment, the user may have a set of goals. A relative importance of the goals with respect to one another may be explicitly specified by the user or inferred (e.g., if the user posts daily about learning a language and rarely posts about losing weight, then a goal of learning the language may be inferred as more important than a goal of losing weight). Accordingly, weights of relative importance may be applied for each goal within the set of goals. A weighted average of increases in successive probabilities of the user making progress over each goal may be utilized to rank content items in order to determine which content item to provide to the user (e.g., a content item likely to cause the user to study a language may be ranked higher than a content item likely to cause the user to lose weight).

DESCRIPTION OF THE DRAWINGS

While the techniques presented herein may be embodied in alternative forms, the particular embodiments illustrated in the drawings are only a few examples that are supplemental of the description provided herein. These embodiments are not to be interpreted in a limiting manner, such as limiting the claims appended hereto.

DETAILED DESCRIPTION

Subject matter will now be described more fully hereinafter with reference to the accompanying drawings, which form a part hereof, and which show, by way of illustration, specific example embodiments. This description is not intended as an extensive or detailed discussion of known concepts. Details that are known generally to those of ordinary skill in the relevant art may have been omitted, or may be handled in summary fashion.

The following subject matter may be embodied in a variety of different forms, such as methods, devices, components, and/or systems. Accordingly, this subject matter is not intended to be construed as limited to any example embodiments set forth herein. Rather, example embodiments are provided merely to be illustrative. Such embodiments may, for example, take the form of hardware, software, firmware or any combination thereof.

1. Computing Scenario

The following provides a discussion of some types of computing scenarios in which the disclosed subject matter may be utilized and/or implemented.

1.1. Networking

Figure 1:
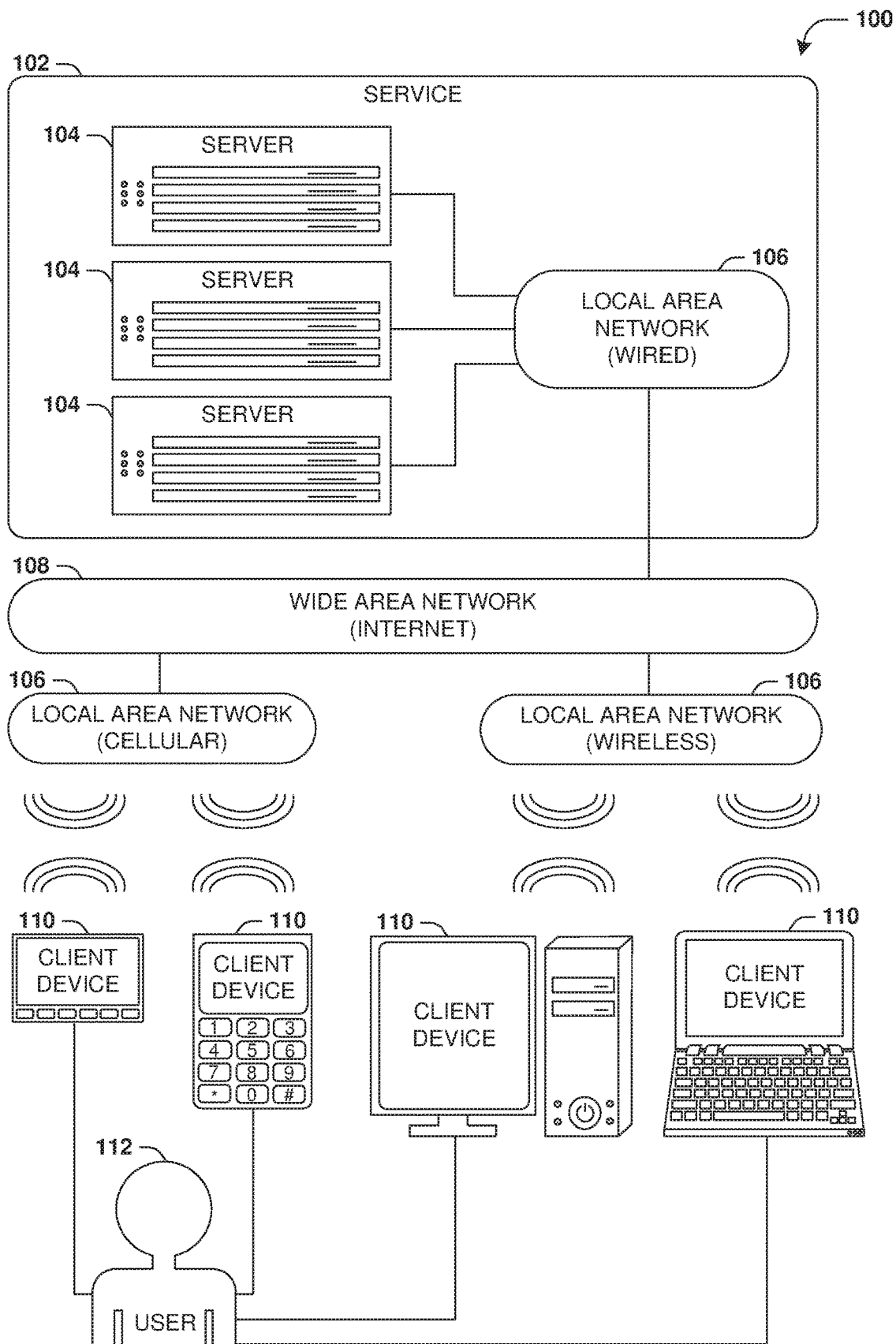
FIG. 1 is an illustration of a scenario involving various examples of networks that may connect servers and clients.

FIG. 1 is an interaction diagram of a scenario 100 illustrating a service 102 provided by a set of servers 104 to a set of client devices 110 via various types of networks. The servers 104 and/or client devices 110 may be capable of transmitting, receiving, processing, and/or storing many types of signals, such as in memory as physical memory states.

The servers 104 of the service 102 may be internally connected via a local area network 106 (LAN), such as a wired network where network adapters on the respective servers 104 are interconnected via cables (e.g., coaxial and/or fiber optic cabling), and may be connected in various topologies (e.g., buses, token rings, meshes, and/or trees). The servers 104 may be interconnected directly, or through one or more other networking devices, such as routers, switches, and/or repeaters. The servers 104 may utilize a variety of physical networking protocols (e.g., Ethernet and/or Fiber Channel) and/or logical networking protocols (e.g., variants of an Internet Protocol (IP), a Transmission Control Protocol (TCP), and/or a User Datagram Protocol (UDP). The local area network 106 may include, e.g., analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. The local area network 106 may be organized according to one or more network architectures, such as server/client, peer-to-peer, and/or mesh architectures, and/or a variety of roles, such as administrative servers, authentication servers, security monitor servers, data stores for objects such as files and databases, business logic servers, time synchronization servers, and/or front-end servers providing a user-facing interface for the service 102.

Likewise, the local area network 106 may comprise one or more sub-networks, such as may employ differing architectures, may be compliant or compatible with differing protocols and/or may interoperate within the local area network 106. Additionally, a variety of local area networks 106 may be interconnected; e.g., a router may provide a link between otherwise separate and independent local area networks 106.

In the scenario 100 of FIG. 1, the local area network 106 of the service 102 is connected to a wide area network 108 (WAN) that allows the service 102 to exchange data with other services 102 and/or client devices 110. The wide area network 108 may encompass various combinations of devices with varying levels of distribution and exposure, such as a public wide-area network (e.g., the Internet) and/or a private network (e.g., a virtual private network (VPN) of a distributed enterprise).

In the scenario 100 of FIG. 1, the service 102 may be accessed via the wide area network 108 by a user 112 of one or more client devices 110, such as a portable media player (e.g., an electronic text reader, an audio device, or a portable gaming, exercise, or navigation device); a portable communication device (e.g., a camera, a phone, a wearable or a text chatting device); a workstation; and/or a laptop form factor computer. The respective client devices 110 may communicate with the service 102 via various connections to the wide area network 108. As a first such example, one or more client devices 110 may comprise a cellular communicator and may communicate with the service 102 by connecting to the wide area network 108 via a wireless local area network 106 provided by a cellular provider. As a second such example, one or more client devices 110 may communicate with the service 102 by connecting to the wide area network 108 via a wireless local area network 106 provided by a location such as the user's home or workplace (e.g., a WiFi (Institute of Electrical and Electronics Engineers (IEEE) Standard 802.11) network or a Bluetooth (IEEE Standard 802.15.1) personal area network). In this manner, the servers 104 and the client devices 110 may communicate over various types of networks. Other types of networks that may be accessed by the servers 104 and/or client devices 110 include mass storage, such as network attached storage (NAS), a storage area network (SAN), or other forms of computer or machine readable media.

1.2. Server Configuration

Figure 2:
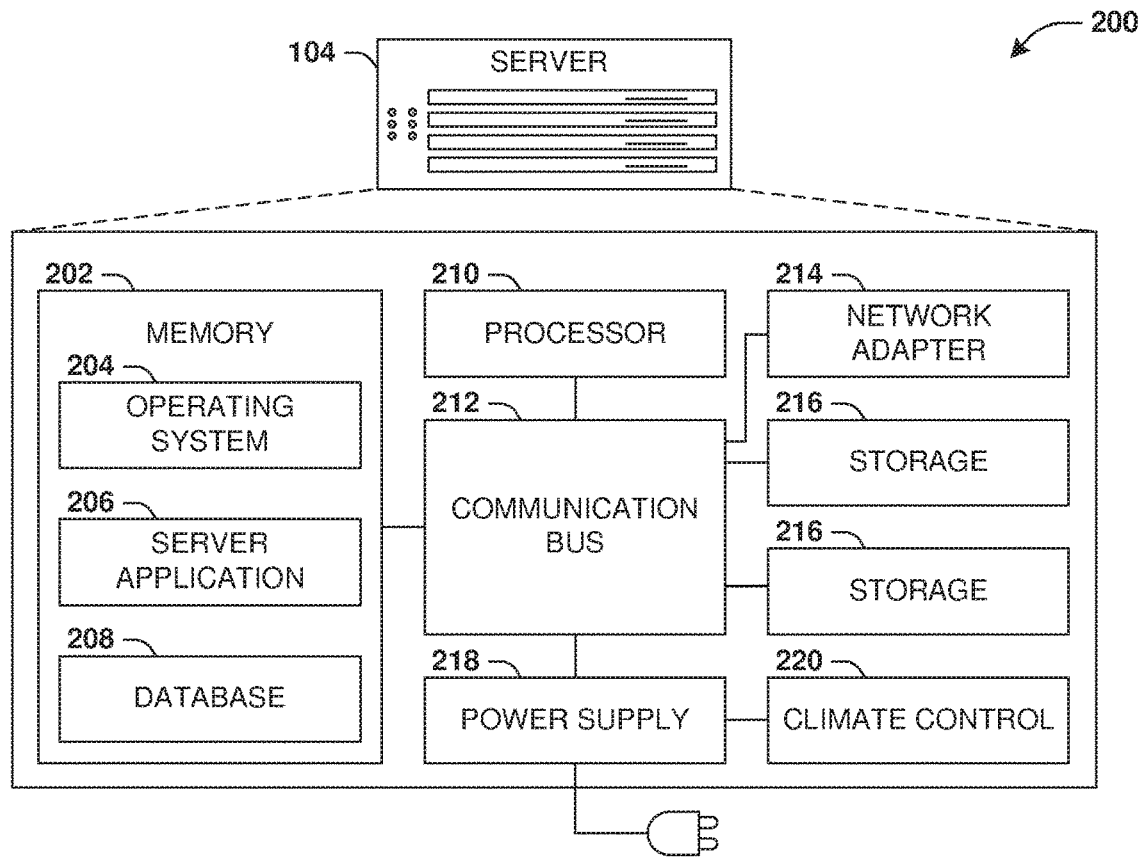
FIG. 2 is an illustration of a scenario involving an example configuration of a server that may utilize and/or implement at least a portion of the techniques presented herein.

FIG. 2 presents a schematic architecture diagram 200 of a server 104 that may utilize at least a portion of the techniques provided herein. Such a server 104 may vary widely in configuration or capabilities, alone or in conjunction with other servers, in order to provide a service such as the service 102.

The server 104 may comprise one or more processors 210 that process instructions. The one or more processors 210 may optionally include a plurality of cores; one or more coprocessors, such as a mathematics coprocessor or an integrated graphical processing unit (GPU); and/or one or more layers of local cache memory. The server 104 may comprise memory 202 storing various forms of applications, such as an operating system 204; one or more server applications 206, such as a hypertext transport protocol (HTTP) server, a file transfer protocol (FTP) server, or a simple mail transport protocol (SMTP) server; and/or various forms of data, such as a database 208 or a file system. The server 104 may comprise a variety of peripheral components, such as a wired and/or wireless network adapter 214 connectible to a local area network and/or wide area network; one or more storage components 216, such as a hard disk drive, a solid-state storage device (SSD), a flash memory device, and/or a magnetic and/or optical disk reader.

The server 104 may comprise a mainboard featuring one or more communication buses 212 that interconnect the processor 210, the memory 202, and various peripherals, using a variety of bus technologies, such as a variant of a serial or parallel AT Attachment (ATA) bus protocol; a Uniform Serial Bus (USB) protocol; and/or Small Computer System Interface (SCI) bus protocol. In a multibus scenario, a communication bus 212 may interconnect the server 104 with at least one other server. Other components that may optionally be included with the server 104 (though not shown in the schematic architecture diagram 200 of FIG. 2)

include a display; a display adapter, such as a graphical processing unit (GPU); input peripherals, such as a keyboard and/or mouse; and a flash memory device that may store a basic input/output system (BIOS) routine that facilitates booting the server 104 to a state of readiness.

The server 104 may operate in various physical enclosures, such as a desktop or tower, and/or may be integrated with a display as an "all-in-one" device. The server 104 may be mounted horizontally and/or in a cabinet or rack, and/or may simply comprise an interconnected set of components. The server 104 may comprise a dedicated and/or shared power supply 218 that supplies and/or regulates power for the other components. The server 104 may provide power to and/or receive power from another server and/or other devices. The server 104 may comprise a shared and/or dedicated climate control unit 220 that regulates climate properties, such as temperature, humidity, and/or airflow. Many such servers 104 may be configured and/or adapted to utilize at least a portion of the techniques presented herein.

1.3. Client Device Configuration

Figure 3:
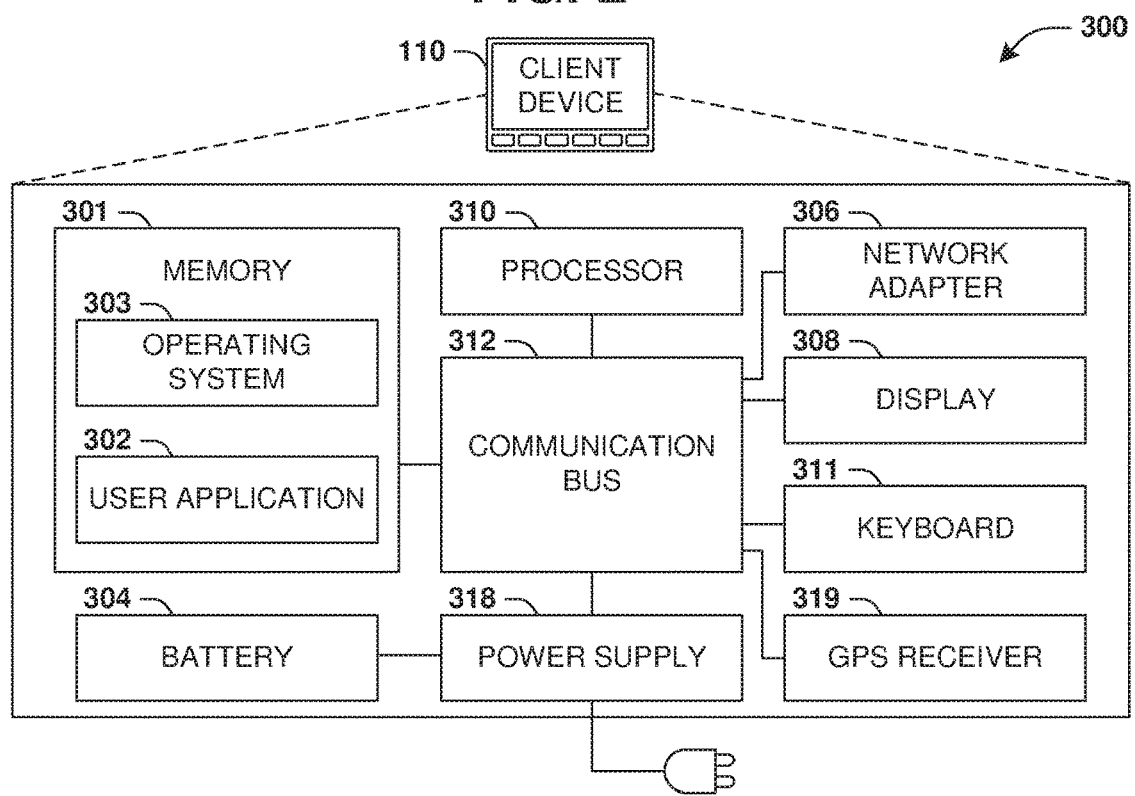
FIG. 3 is an illustration of a scenario involving an example configuration of a client that may utilize and/or implement at least a portion of the techniques presented herein.

FIG. 3 presents a schematic architecture diagram 300 of a client device 110 whereupon at least a portion of the techniques presented herein may be implemented. Such a client device 110 may vary widely in configuration or capabilities, in order to provide a variety of functionality to a user such as the user 112. The client device 110 may be provided in a variety of form factors, such as a desktop or tower workstation; an "all-in-one" device integrated with a display 308; a laptop, tablet, convertible tablet, or palmtop device; a wearable device mountable in a headset, eyeglass, earpiece, and/or wristwatch, and/or integrated with an article of clothing; and/or a component of a piece of furniture, such as a tabletop, and/or of another device, such as a vehicle or residence. The client device 110 may serve the user in a variety of roles, such as a workstation, kiosk, media player, gaming device, and/or appliance.

The client device 110 may comprise one or more processors 310 that process instructions. The one or more processors 310 may optionally include a plurality of cores; one or more coprocessors, such as a mathematics coprocessor or an integrated graphical processing unit (GPU); and/or one or more layers of local cache memory. The client device 110 may comprise memory 301 storing various forms of applications, such as an operating system 303; one or more user applications 302, such as document applications, media applications, file and/or data access applications, communication applications such as web browsers and/or email clients, utilities, and/or games; and/or drivers for various peripherals. The client device 110 may comprise a variety of peripheral components, such as a wired and/or wireless network adapter 306 connectible to a local area network and/or wide area network; one or more output components, such as a display 308 coupled with a display adapter (optionally including a graphical processing unit (GPU)), a sound adapter coupled with a speaker, and/or a printer; input devices for receiving input from the user, such as a keyboard 311, a mouse, a microphone, a camera, and/or a touch-sensitive component of the display 308; and/or environmental sensors, such as a global positioning system (GPS) receiver 319 that detects the location, velocity, and/or acceleration of the client device 110, a compass, accelerometer, and/or gyroscope that detects a physical orientation of the client device 110. Other components that may optionally be included with the client device 110 (though not shown in the schematic architecture diagram 300 of FIG. 3) include one or more storage components, such as a hard disk drive, a solid-state storage device (SSD), a flash memory device, and/or a magnetic and/or optical disk reader; and/or a flash memory device that may store a basic input/output system (BIOS) routine that facilitates booting the client device 110 to a state of readiness; and a climate control unit that regulates climate properties, such as temperature, humidity, and airflow.

The client device 110 may comprise a mainboard featuring one or more communication buses 312 that interconnect the processor 310, the memory 301, and various peripherals, using a variety of bus technologies, such as a variant of a serial or parallel AT Attachment (ATA) bus protocol; the Uniform Serial Bus (USB) protocol; and/or the Small Computer System Interface (SCI) bus protocol. The client device 110 may comprise a dedicated and/or shared power supply 318 that supplies and/or regulates power for other components, and/or a battery 304 that stores power for use while the client device 110 is not connected to a power source via the power supply 318. The client device 110 may provide power to and/or receive power from other client devices.

In some scenarios, as a user 112 interacts with a software application on a client device 110 (e.g., an instant messenger and/or electronic mail application), descriptive content in the form of signals or stored physical states within memory (e.g., an email address, instant messenger identifier, phone number, postal address, message content, date, and/or time) may be identified. Descriptive content may be stored, typically along with contextual content. For example, the source of a phone number (e.g., a communication received from another user via an instant messenger application) may be stored as contextual content associated with the phone number. Contextual content, therefore, may identify circumstances surrounding receipt of a phone number (e.g., the date or time that the phone number was received), and may be associated with descriptive content. Contextual content, may, for example, be used to subsequently search for associated descriptive content. For example, a search for phone numbers received from specific individuals, received via an instant messenger application or at a given date or time, may be initiated. The client device 110 may include one or more servers that may locally serve the client device 110 and/or other client devices of the user 112 and/or other individuals. For example, a locally installed webserver may provide web content in response to locally submitted web requests. Many such client devices 110 may be configured and/or adapted to utilize at least a portion of the techniques presented herein.

2. Presented Techniques

Techniques are provided for content item selection for goal achievement. A user may consume content through a variety of services (e.g., an email service), user interfaces, applications (e.g., a social network application), and websites provided by content providers. A content provider may select content items to provide to the user to supplement the content that users would normally be provided. For example, the user may be viewing a social network feed provided by a social network content provider through a social network application. The social network feed may be populated with social network posts created by friends of the user. In addition, the social network content provider may evaluate a set of content items using a particular objective in order to select a content item to additionally provide to the user through the social network feed. The objective may correspond to selecting content items that will have a high probability of user engagement in order to keep the user engaged with the social network feed for as long as possible so that the user can be provided with revenue generating opportunities such as advertisements, subscription offers, etc. Unfortunately, these types of content items and objectives of addiction and increasing revenue may not benefit the user. Thus, there is a need for selecting content items that will benefit the user, such as content items that will inspire and/or motivate the user to achieve goals.

Accordingly, as provided herein, a content recommendation component (e.g., a component implemented by hardware, software, or combination thereof) is configured to select content items to provide to users based upon an objective of increasing a likelihood that the users will make progress towards their goals based upon the users consuming the content items. In particular, goals of users are identified. For example, a user may explicitly define a goal (e.g., save for a vacation) or the goal may be inferred based upon an evaluation of various user signals (e.g., the user sends a message to a friend about wanting to take a vacation but needing to save for the vacation). Content items are then provided to the users, and feedback is obtained as to whether the users made progress towards their goals. For example, a beach vacation video may be provided to the user through a social network feed.

The user may have registered and provided opt-in consent for the content recommendation component to have access to certain data sources, such as an email account, bank statements, user location data, social network activity, website browsing history, etc. In this way, the content recommendation component may evaluate feedback from the data sources to determine whether the user made progress towards saving for the vacation (e.g., a bank statement may indicate that the user has increased savings by $2,000). Information about users, goals of each user, what content items have been provided to what users, and goal progress of each users may be tracked and/or used to cluster similar users with similar goals. This information is also used to train a model (e.g., a machine learning model) used by the content recommendation component to select content items to provide to users with the objective of increasing a likelihood that the users will make progress towards their goals based upon the users consuming the content items.

As part of training the model, statistical filtering is performed to filter a set of content items to identify those content items that correlate to goal progress for groups/clusters of users. For example, the statistical filtering may identify a particular content item that was provided to a group of users that made progress towards saving for a vacation. Thus, those content items may be marked as having a correlation with the goal of saving towards a vacation for those types of users within the group of users. However, correlation may not always be the same as causation where the viewing of a content item by a user is an actual causation factor for the user to perform progress towards the goal. Accordingly, causation testing, such as A/B testing, may be performed where some users with the vacation savings goal are provided with a content item and other users with the vacation savings goal are not provided with the content item. In this way, the causation testing can be used to train the model (e.g., modify parameters, weights of parameters, algorithms/functions, analysis, etc. of the model) to identify whether users viewing the content item was a causation factor for those users making progress towards saving for a vacation or not (e.g., users may have saved for the vacation even though they were not provided with the content item, and thus the content item may not be a good candidate to provide to users to inspire those users to save for a vacation compared to other content items, and further parameters/functions used to select the content item may have relative weights of importance/accuracy decreased).

Once trained, the content recommendation component can utilize the model to select a content item to provide to a user in order to increase a probability that the user will be inspired and/or motivated by the content item to make progress towards a goal. In this way, the model is used by the content recommendation component for a practical application of identifying content items to provide to users in order to achieve a particular objective of increasing a probability that the users make progress towards their goals.

Figure 4:
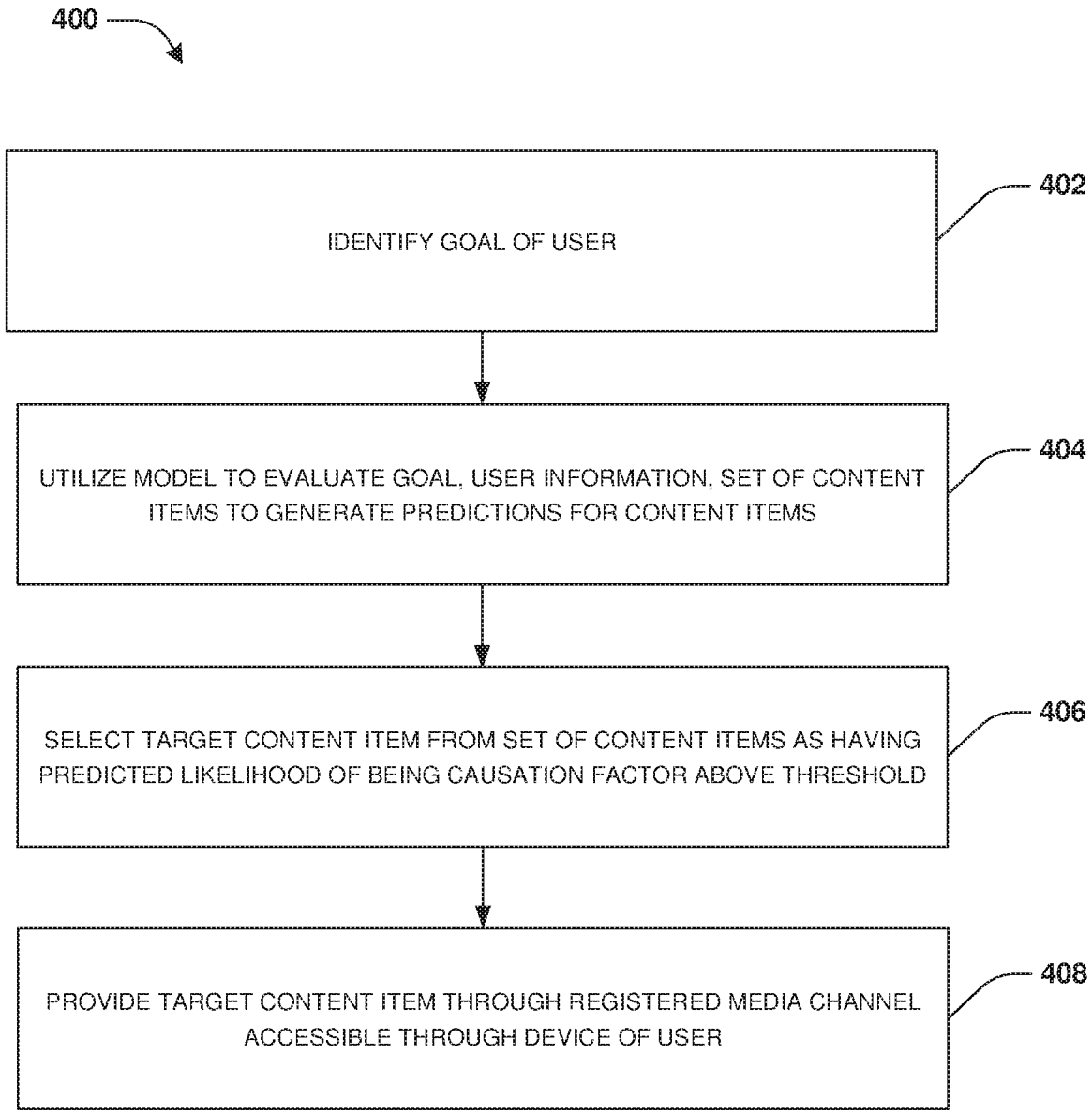
FIG. 4 is a flow chart illustrating an example method for content item selection for goal achievement.

An embodiment of content item selection for goal achievement is illustrated by an example method 400 of FIG. 4. At 402, a goal of a user may be identified. In an embodiment, the user may register with a content recommendation component, such as a service configured to provide content items to users. The user may utilize a user interface to input user information, such as an age of the user, a gender, a work location, a home location, a media preference (e.g., a preference to use a particular video streaming service, the use of a particular social network profile, an email service and account, etc.), and/or a wide variety of other information about the user. The user may utilize the user interface to input the goal of the user. For example, the user may specify a goal to achieve a high score in a racing videogame. In an embodiment, the user may select a goal from a set of predefined goals (e.g., achieve a high score in a videogame). The user may further define the selected goal (e.g., specify the name of the videogame, a score threshold, a time duration within which the score threshold should be reached such as within a month, and/or other parameters of the goal). The user may break the goal down into multiple steps, such as a first sub-goal step to save money to buy the videogame, a second sub-goal step to install and practice at the videogame, and a third sub-goal step to beat a particular score in the videogame. In an embodiment, the user information, such as age data, gender data, home location data, work location data, and media preference data of users may be stored within a user repository accessible to the content recommendation component.

In an embodiment, the user does not register with the content recommendation component, and thus the user is identified by the content recommendation component for the purpose of providing content items to the user for achieving a goal of the user (e.g., the user may log into an email account hosted by an email service utilizing the content recommendation component, and thus the user may be identified for the purpose of providing content items to the user, such as through an email user interface, for achieving a goal of the user). The user information may be automatically collecting from various content sources, such as from email content, an email account profile, global positioning system (GPS) location data indicative of where the user resides and where the user works, publically available social network posts, calendar entries maintained with the emails service, etc.

In an embodiment, the goal of the user may be inferred from various user signals. For example, the content recommendation component may evaluate emails, social network posts, queries submitted by the user, browsing history, locational data, receipts, and/or a wide variety of information from various data sources to infer the goal (e.g., the user may create a social network post about buying a videogame, and then the user may submit a search query for how to obtain a highest score in the videogame).

Various types of goals may be predefined and/or user defined. In an embodiment, a goal may comprise a health goal, such as achieving or maintaining a healthy weight, blood pressure level, blood sugar level, or exercise routine, taking medicine as prescribed, monitoring health on a prescribed schedule, establishing or maintaining healthy eating habits, etc. In an embodiment, a goal may comprise a financial goal, such as saving for retirement, buying a home, remodeling a home, starting a business, investing, finding a new or better job, advancing in a current job, etc.

In an embodiment, a goal may comprise an education goal, such as enrolling in or completing an online course or another course of study, obtaining acceptance to a college or graduate school, improving grades in school, learning a skill, learning a language, etc. In an embodiment, the goal may comprise a relationship goal, such as dating, marriage, maintaining a healthy marriage, finding new friends, maintaining healthy friendships, developing or maintaining healthy relationships with immediate or extended family, etc. In an embodiment, a goal may comprise a lifestyle goal, such as embracing a new style in fashion, refining an old style in fashion, taking an enjoyable vacation, establishing or maintaining habits that are good for the environment, getting involved in a cause, becoming a sports fan, adopting a pet, improving athletic performance, etc.

In an embodiment, a time limit may be applied to the goal by the content recommendation component. The time limit may be inferred or specified by the user. In an example, the user specifies that the user wants to beat the score threshold by the end of summer before school starts. In another example, the user may have a goal to see the next winter Olympics in person, and thus a time limit may be inferred by the content recommendation component as to being as date at which the next winter Olympics end.

At 404, the content recommendation component utilizes a model to evaluate the goal (e.g., the goal to beat the score threshold in the racing videogame), the user information (e.g., the age of the user, the gender of the user, media preferences of the user, and/or a variety of demographic information about the user), and a set of content items (e.g., text, images, videos, etc., along with metadata of content items and relationships amongst content items) to generate predictions for content items of how likely each content item will be a causation factor of the user making progress towards the goal in response to the user being provided with each content item. In an embodiment, the content recommendation component analyzes content items stored within a media repository. The content recommendation component may store metadata about content items (e.g., an author of a content item, a date the content item was created, a type of content item, a theme of a content item, a topic of a content item, a color scheme of a content item, actors portrayed by a content item, people and objects depicted by a content item, etc.) within the media repository. The content recommendation component may store relationships between content items corresponding to overlap of authorship data, themes data, location data, actors data, users experiencing content items, times of users experiencing content items, and/or other similarities/overlaps of metadata associated with content items. In this way, the metadata and relationships may be utilized by the content recommendation component and model for selecting content items to provide to users (e.g., if a content item caused a user to make progress towards a goal, then metadata and relationships of the content item may be used to identify other similar content items to subsequently provide to the user to cause the user to make further progress towards the goal and/or to other users with a similar goal).

In an embodiment, the model also evaluates other information, such as aggregated historical data of other users. For example, progress of users towards their goals may be tracked by the content recommendation component. Content items provided to those users, the progress towards their goals, and/or user information about the users may be used to cluster the users into clusters (groups). A cluster may comprise similar users with similar goals, along with content items provided to those users and the progress of each user made towards their goal. Accordingly historical data may be generated for each user. The historical data relates to content items provided to each user and goal progress data. In this way, a cluster of users that are similar to the user and have similar goals as the user may be identified. An aggregate of historical data of those users within the cluster may be utilized as input into the model for generating the predictions for content items, ranking the content items based upon the predictions, and/or selecting a target content item to provide to the user. In an embodiment, the model may map a combination of user, item, and goal to different probabilities that a user will make progress towards a goal if a content item is provided to that user.

The aggregated historical data may be used to train the model to more accurately predict what content items will inspire and/or motivate certain types of users to make progress to particular goals. For example, statistical filtering is performed upon the set of content items based upon the aggregated historical data to identify content items that correlate to goal progress for groups (clusters) of users. A group of users may comprise users that made progress towards a goal and who were also provided with a particular content item. Thus, the statistical filtering can identify correlations between goal progress and content items being provided to users. However, some correlations may not actually be the same as causation, such as where a content item was provided to a user that made progress towards a goal, but not because of being provided with the content item and would have made progress towards the goal even if not provided with the content item.

Accordingly, causality testing, such as A/B testing, is performed to train the model on not just correlations but also on causation. In particular, causality testing may be performed for a content item by tracking whether a first set of users provided with the content item made progress towards the goal and whether a second set of users not provided with the content item made progress towards the goal. If a threshold amount of users within the second set of users made progress towards the goal (e.g., or if certain percentage of users within the second set of users made progress towards the goal in relation to a percentage of users within the first set of users), then the model may be trained to understand that the content item may not be a causation factor for users to make progress towards the goal (e.g., parameters and/or functions used by the model to select the content item may be discounted, such as by having a relative weight of importance decreased to indicate that the parameters and/or functions are relatively less accurate). In this way, the model may be trained to identify content items that cause users to make progress towards certain goals.

Once trained, the model is utilized, at 404, to generate the predictions for the content items of how likely each content item will be a causation factor of the user making progress towards the goal in response to the user being provided with each content item. In an embodiment of generating the predictions, the model may comprise a function with an input of an item input (e.g., metadata and relationships of the content item to other content items), a user input (e.g., the user information of the user), and a goal input (e.g., a description and parameters of the user having the goal of reaching the score threshold). The output of the function is an increase in probability that the user will make progress towards the goal if provided with the content item, which is based upon a difference between a probability that the user makes progress towards the goal if provided with the content item and a probability that the user makes progress towards the goal if the user is not provided with the content item. In this way, the increase in probability may be used as a ranking factor related to a predicted likelihood that the content item is a causation factor of the user making progress towards the goal (e.g., the more likely the content item is a causation factor, the larger the ranking factor).

In an embodiment, other systems (components) may be utilized for ranking the content items (e.g., the content items are ranked so that a highest ranked content item may be provided to the user). For example, the content recommendation component may utilize the objective of inspiring and/or motivating the user to make progress towards the goal. Another system may utilize a different objective, such as an objective to maximize a likelihood of the user engaging with content items or an objective to maximize revenue generated from the user interacting with content items, to additionally rank the content items. The ranks (ranking factors) output by the systems may be taken into account, such as aggregated, for ranking content items to determine which content item (e.g., a highest ranked content item) to provide to the user for inspiring and/or motivating the user to make progress towards the goal.

At 406, a target content item is selected, by the content recommendation component, from the set of content items based upon the target content item having a predicted likelihood of being the causation factor (e.g., a ranking factor) above a threshold. In an embodiment, the threshold corresponds to a largest predicted likelihood of being the causation factor (e.g., a largest ranking factor). In an example, a motivational speech about putting forth your best effort in all aspects of life such as personal hobbies may be selected as the target content item based upon the motivational speech having a largest predicted likelihood of being the causation factor (e.g., a largest ranking factor). In an embodiment, the content item may comprise a video, text, a link to a website, a recommendation (e.g., a recommendation of taking a break from consuming content), an image, a game, etc.

In an embodiment, a risk tolerance of the user is taken into account when selecting the target content item. For example, the user may have a risk tolerance for an outcome of failing to achieve the goal (e.g., if the goal is to obtain a raise at work, then the user may have a 10% risk tolerance of losing a job from asking for the raise in relation to obtaining a $5 k raise). Accordingly, the risk tolerance is utilized for selecting the target content item.

At 408, the target content item is provided through a registered media channel associated with a device of the user. The registered media channel may correspond to a media preference specified by the user, such as an email account (e.g., the content item may be provided through an email user interface or through an email), a social network profile (e.g., the content item may be provided through a social network user interface or as a post), a phone number (e.g., the content item may be provided as a text message), a streaming service subscribed to by the user (e.g., the content item may be provided as a recommended video to watch), a videogame console account (e.g., a content item may be provided as a recommendation through a videogame console interface to try a videogame), etc. Subsequent to providing the target content item to the user, a follow-up recommendation of an activity associated with the target content item and/or the goal of the user may be provided (e.g., if the target content item comprised the motivational speech about personal hobbies, then the recommendation may recommend an activity of starting another hobby that was discussed in the motivational speech).

In an embodiment, progress of the user achieving the goal is tracked through goal measurement feedback channels. A goal measurement feedback channel may correspond to a data source from which the content recommendation component can retrieve data indicative of whether the user made progress towards achieving the goal. For example, the goal measurement feedback channel may correspond to a phone (e.g., GPS data transmitted by the phone over a network to the content recommendation component), a smart scale (e.g., a weight of the user transmitted by the smart scale over a network to the content recommendation component), a smart refrigerator (e.g., an indication of what food the user is storing within the smart refrigerator), a bank account statement (e.g., a bank statement accessible through a website or banking service for which the user has provided access credentials to the content recommendation component), a receipt (e.g., a receipt within an email of an email account for which the user has provided access credentials to the content recommendation component), a social network service (e.g., a social network post by the user), an image sharing service (e.g., an image shared by the user), a videogame console account (e.g., an indication of games current owned by the user, high scores achieved by the user, etc.), email (e.g., an exchange of emails between the user and a cousin), a wearable exercise device such as a smart watch (e.g., a number of steps taken by the user within a day), medical and pharmacy records (e.g., an indication that the user refilled a prescription), etc. Explicit opt-in consent may be obtained from the user to obtain access to certain goal measurement feedback channels (e.g., consent to access medical records, bank statements, emails, etc.).

In an embodiment, a goal measurement feedback channel may be explicitly defined and set up by the user, such as where the user utilizes a user interface to provide the content recommendation component with access to bank account statements accessible through a website of a bank. In an embodiment, a goal measurement feedback channel may be inferred by the content recommendation component, such as where a publically available social network posts by the user may be obtained as goal progress feedback of the user. In an embodiment, the goal measurement feedback channel may correspond to user input of the user, output of device equipment (e.g., a phone, a watch, a treadmill, a scale, a vehicle, etc.), and/or user input by a third party, such as a parent, a doctor, a pharmacist, a financial advisor, etc.

In an embodiment, the user may have multiple goals, such as a goal to save for a car, the goal to beat the score threshold in the racing videogame, a goal to keep in better contact with a cousin, etc. Weights of relative importance for each goal may be applied to the goals of the user. In an embodiment, the weights may be explicitly set by the user (e.g., the user may rank the importance of each goal). In an embodiment, the weights may be infer by the content recommendation component. For example, a relatively larger weight may be assigned to a goal that the user routinely posts about on a social network compared to another goal that the user posted about once through the social network. A weighted average of increases in successive probabilities of the user making progress over each goal may be utilized to rank content items to determine which content items to provide to the user so that the user has the highest probability of making progress towards goals that are more important to the user in response to being provided with selected content items.

Figure 5:
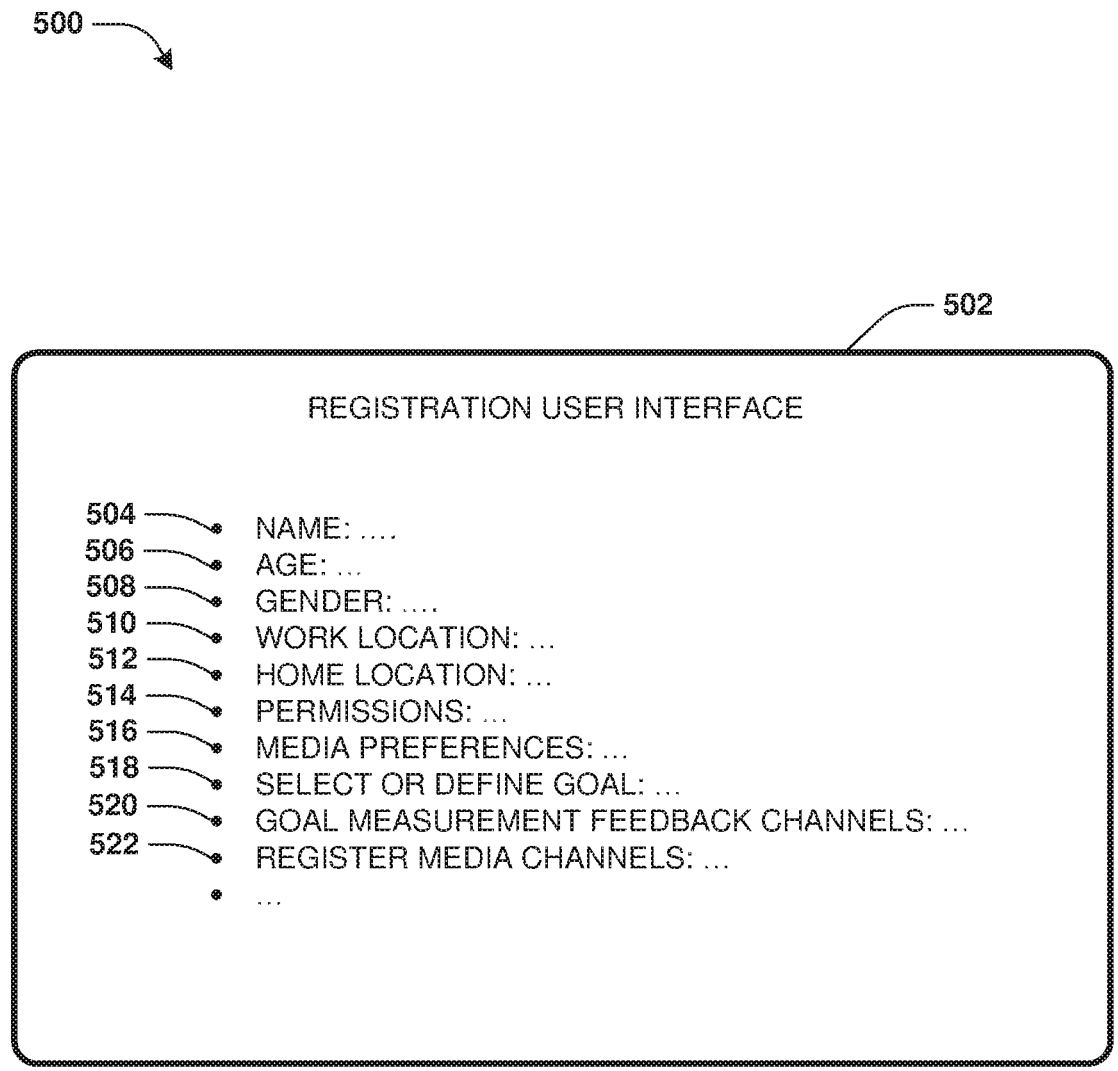
FIG. 5 is a component block diagram illustrating an example system for content item selection for goal achievement, where a registration user interface is utilized to receive user and goal information.

FIG. 5 illustrates a system 500 for content item selection for goal achievement. A user may access a registration user interface 502 utilizing a computing device, such as through a mobile application or website. The registration user interface 502 may be associated with a content recommendation component configured to provide content items to the user with an objective of the user making progress towards a goal. The user may utilize the registration user interface 502 to register with the content recommendation component. The user may utilize a name input user interface element 504 to input a name of the user. The user may utilize an age input user interface element 506 to input an age of the user. The user may utilize a gender user interface element 508 to input a gender of the user. The user may utilize a work location user interface element 510 to input a work location of the user where the user is employed. The user may utilize a home location user interface element 512 to input a home location of the user where the user resides.

The user may utilize a permissions user interface element 514 to provide explicit opt-in consent for the content recommendation component to access certain data sources to obtain information used to identify goals of the user, user information about the user, and/or goal progress of the user. The user may utilize the permissions user interface element 514 to specify credentials needed to access the data sources, such as an email account login and password, a bank website login and password, access information for a smart thermostat within a home of the user, etc. The user may utilize a media preferences user interface element 516 to specify preferences of what types of content items the user prefers, such as images, videos, messages, links to websites, etc. The user may utilize a goal definition user interface element 518 to select a predefined goal, further define or modify the predefined goal, break the predefined goal into sub-goals, and/or specify a user defined goal. The user may utilize a goal measurement feedback channels user interface element 520 to specify data sources from which the content recommendation component is to obtain goal progress data, such as information about an email account of the user, information about a smart scale, information about an exercise watch, etc. The user may utilize a register media channels user interface element 522 to specify applications, websites, email accounts, social network profiles, a phone number for text messages, a videogame console account, a media streaming service, and/or a variety of other media channels through which the user prefers to receive content items from the content recommendation component.

Figure 6:
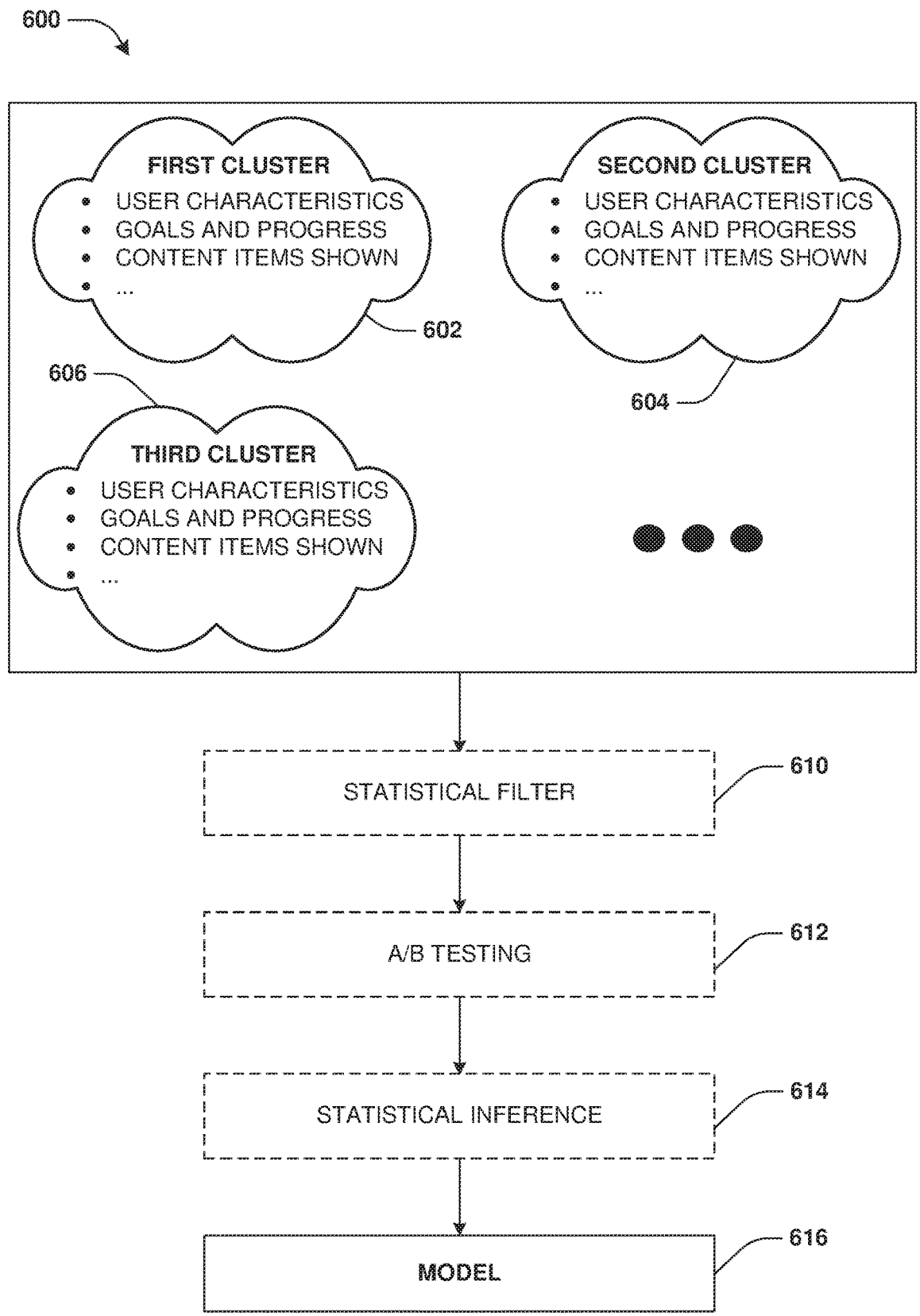
FIG. 6 is a component block diagram illustrating an example system for content item selection for goal achievement, where a model to generated and trained.

FIG. 6 illustrates a system 600 for content item selection for goal achievement. A content recommendation component may be configured to train a model 616 for selecting content items to provide to users based upon the content items having relatively larger likelihoods of being causation factors for the users to make progress towards their goals. The content recommendation component may be configured to generate clusters, such as a first cluster 602, a second cluster 604, a third cluster 606, and/or other clusters. The generation recommendation component may generate the clusters based upon at least one of user characteristics/ information of users (e.g., create a cluster of similar users, such as users with similar ages, locations, occupations, etc.), goals of users (e.g., create a cluster of users with similar goals such as users that have a weight loss goal over winter break), goal progress (e.g., create a cluster of users that made similar progress towards a goal), and/or content items provided to users (e.g., create a cluster of users provided with the same content item in order to inspire/motivate the users to make progress towards a goal). Any number of these factors or combinations thereof may be used to cluster users.

As part of training the model 616, the content recommendation component performs statistical filtering 610 for content items to identify content items that correlate to goal progress for groups of users. For example, the content recommendation component may evaluate the first cluster 602 to determine if users, provided with a particular content item, made progress towards a weight loss goal. If the statistical filter 610 determines that the user generally make progress towards their weight loss goals after being provided with the content item, then the content item and the weight loss goal may be correlated together.

Because correlation between the content item and goal progress towards the weight loss goal may not equate to the content item being provided to the users as a causation factor that caused the users to lose weight (e.g., the users would have lost weight regardless of whether the users were provided with the content item), the content recommendation component may perform causation testing, such as A/B testing 612. The A/B testing 612 may be performed to track whether a first set of users provided with the content item made progress towards the weight loss goal and whether a second set of users not provided with the content item made progress towards the weight loss goal. If a proportionally greater number of users within the first set of users made progress towards the weight loss goal than users within the second set of users that made progress towards the weight loss goal, then the content item may be determined to be a causation factor for the users making progress towards the weight loss goal. Otherwise, the content item may not be determined to be the causation factor. In this way, the content recommendation component may create statistical inferences 614 of which content items will cause certain types of users to make progress towards particular goals. The statistical inferences 614 are used by the content recommendation component to train the model 616.

Figure 7:
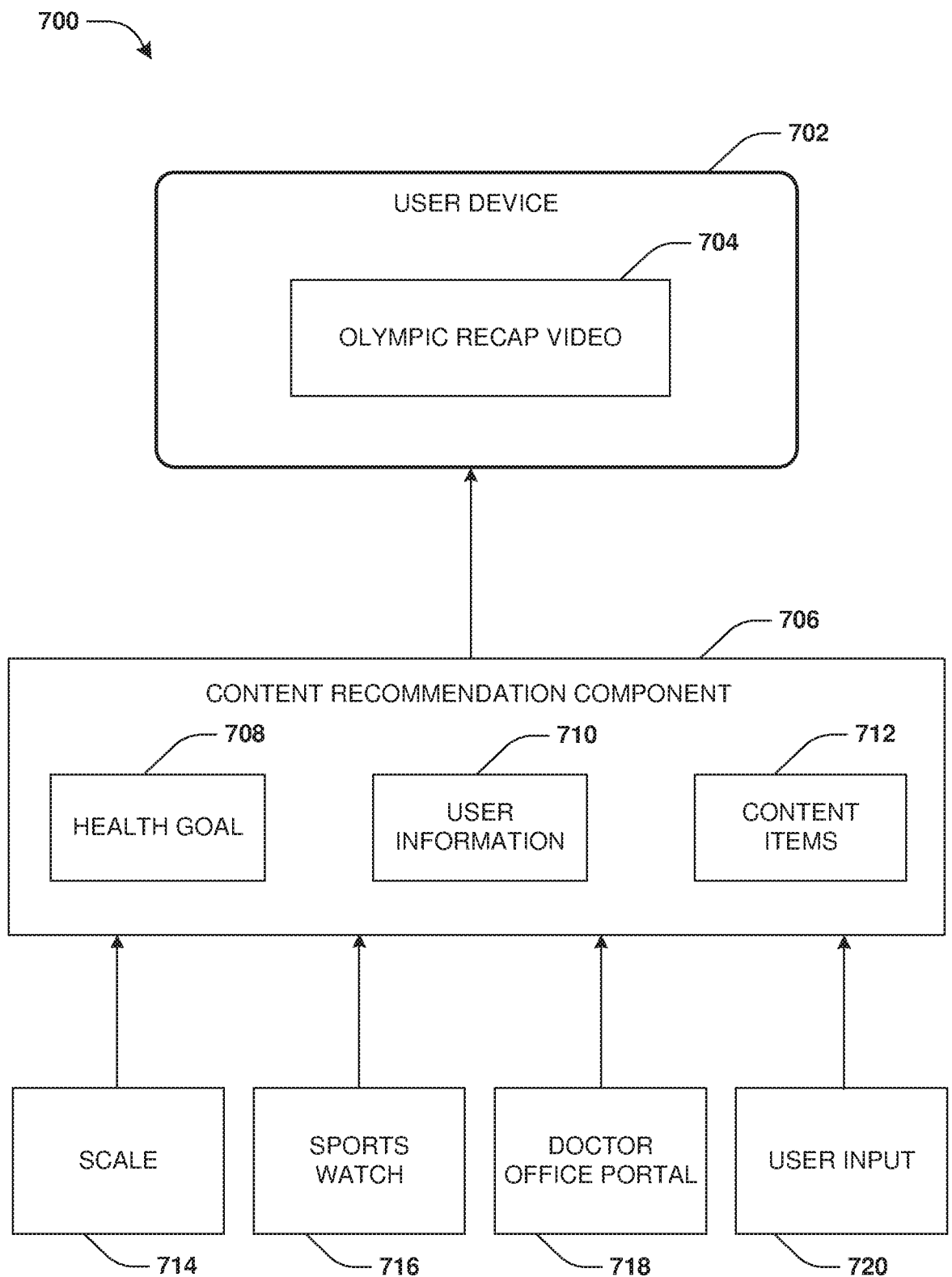
FIG. 7 is a component block diagram illustrating an example system for content item selection for goal achievement, where a model is utilized to select a content item to provide to a user having a health goal.

FIG. 7 illustrates a system 700 for content item selection for goal achievement. A user may utilize a user device 702 (e.g., a mobile phone, a smart device, a laptop, a videogame console, a smart television, etc.) to access a media channel registered with a content recommendation component 706. For example, the user may utilize the user device 702 to access a social network profile of the user. The content recommendation component 706 may receive a notification that the user is accessing the social network profile. In an embodiment, the user may have previously register with the content recommendation component 706. The user may have provided the content recommendation component 706 with an indication that the user is trying to gain 10 lbs of muscle mass over the summer as a health goal 708 of the user. The user may have provided the content recommendation component 706 with user information 710, such as a current weight, an age, information about how to access a smart scale 714 for weight measurement information of the user, information about how to access information from a sports watch 716 for obtaining exercise information from the sports watch 716, explicit opt-in consent to obtain information from a doctor's office health portal 718, and/or a variety of other information.

The content recommendation component 706 may utilize a model (e.g., model 616 of FIG. 6) to evaluate the health goal 708 of gaining 10 lbs of muscle mass over the summer, the user information 710, and a set of content items 712 (e.g., images, videos, links to websites, recommendations, text, etc.) to generate predictions for the content items of how likely each content item will be a causation factor of the user making progress towards the health goal 708 in response to the user being provided with each content item. For example, the model may output an increase in probability that the user will make progress towards the health goal 708 if provided with an Olympic recap video 704 than a probability that the user makes progress towards the health goal 708 without being provided with the Olympic recap video 704. The increase in probability may relate to how strong of a causation factor the Olympic recap video 704 is towards inspiring/motivating the user to make progress towards the health goal 708, which may be utilized as a ranking factor. In response to the Olympic recap video 704 having a predicted likelihood of being the causation factor above a threshold (e.g., a larger predicted likelihood/ranking factor than other content items), the content recommendation component 706 displays the Olympic recap video 704 through a social network feed of the social network profile being accessed by the user.

Progress of the user towards the health goal 708 in response to being provided with the Olympic recap video 704 may be tracked as feedback for further training the model and/or for subsequently selecting content items to provide to the user. For example, the content recommendation component 706 may obtain weight data from the smart scale 714 over a network, a daily step count of the user from the sports watch 716 over the network, muscle mass data accessible through the doctor's office health portal 718, data input as user input 720 by the user, and/or other goal progress information over measurement feedback channels. In an example, parameters and/or statistical analysis performed by the model may be modified based upon whether the goal progress information indicates that the user did or did not make progress towards the health goal 708 after watching the Olympic recap video 704.

Figure 8:
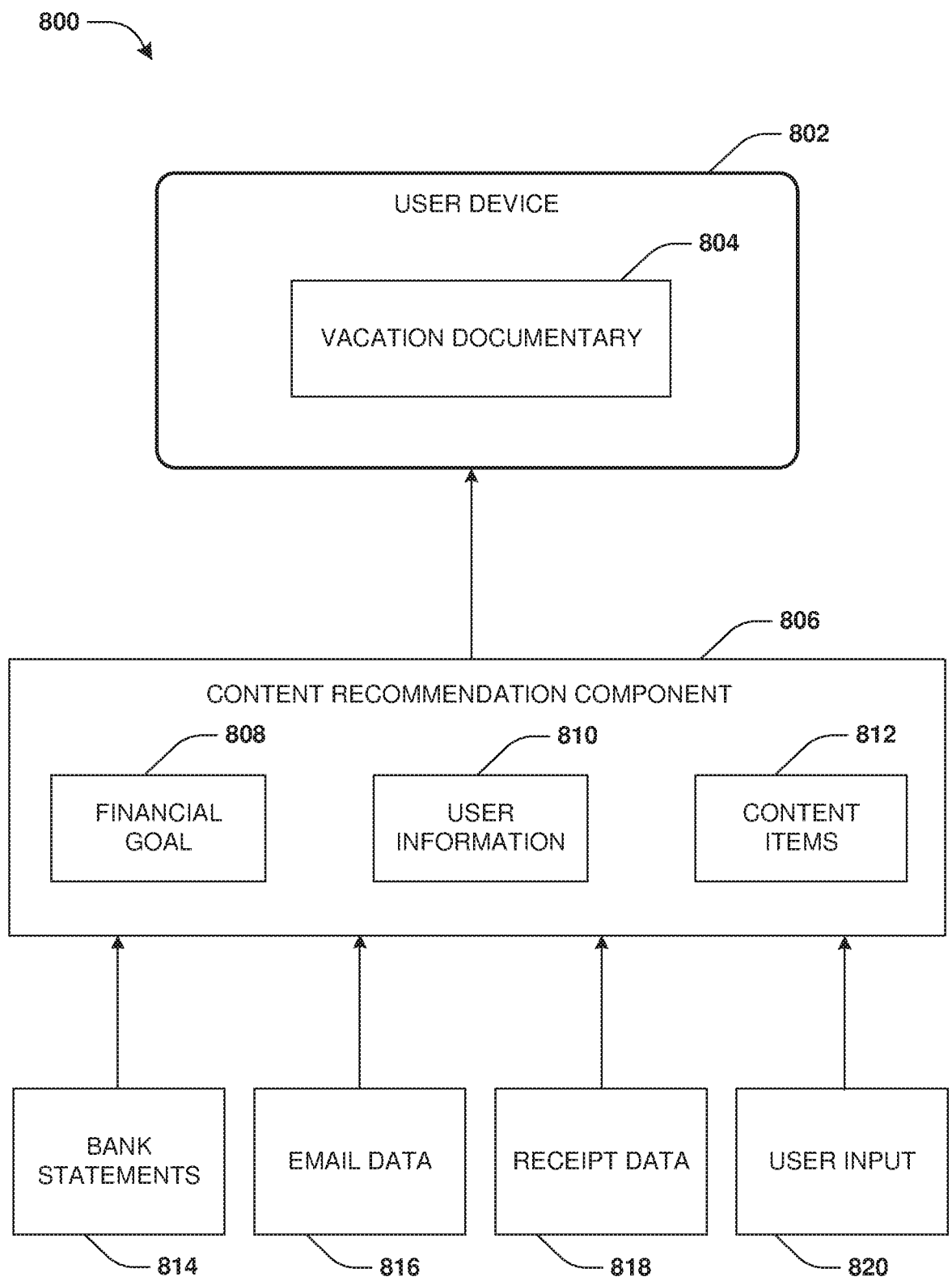
FIG. 8 is a component block diagram illustrating an example system for content item selection for goal achievement, where a model is utilized to select a content item to provide to a user having a financial goal.

FIG. 8 illustrates a system 800 for content item selection for goal achievement. A user may utilize a user device 802 (e.g., a mobile phone, a smart device, a laptop, a videogame console, a smart television, etc.) to access a media channel registered with a content recommendation component 806. For example, the user may utilize the user device 802 to access a video streaming service. The content recommendation component 806 may receive a notification that the user is accessing the video streaming service. In an embodiment, the user may have previously register with the content recommendation component 806. The user may have provided the content recommendation component 806 with an indication that the user is trying to save for a vacation as a financial goal 808. The user may have provided the content recommendation component 806 with user information 810, such as an income level, a current savings account balance, an age, explicit opt-in consent to obtain information about banks statements 814 of the user, explicit opt-in consent to obtain email data 816 from an email account of the user, explicit opt-in consent to obtain receipt data 818 of the user, and/or a variety of other information.

The content recommendation component 806 may utilize a model (e.g., model 616 of FIG. 6) to evaluate the financial goal 808 of saving for a vacation, the user information 810, and a set of content items 812 (e.g., images, videos, links to websites, recommendations, text, etc.) to generate predictions for the content items of how likely each content item will be a causation factor of the user making progress towards the financial goal 808 in response to the user being provided with each content item. For example, the model may output an increase in probability that the user will make progress towards the financial goal 808 if provided with a vacation documentary 804 than a probability that the user makes progress towards the financial goal 808 without being provided with the vacation documentary 804. The increase in probability may relate to how strong of a causation factor the vacation documentary 804 is towards inspiring/motivating the user to make progress towards the financial goal 808, which may be utilized as a ranking factor. In response to the vacation documentary 804 having a predicted likelihood of being the causation factor above a threshold (e.g., a larger predicted likelihood/ranking factor than other content items), the content recommendation component 806 displays the vacation documentary 804 through a video streaming service.

Progress of the user towards the financial goal 808 in response to being provided with the vacation documentary 804 may be tracked as feedback for further training the model and/or for subsequently selecting content items to provide to the user. For example, the content recommendation component 806 may obtain bank statements 814 (e.g., has the user increased an amount of money in a savings account), email data 816 (e.g., has the user received or sent emails regarding vacations, saving money, spending money, etc.), receipt data 818 (e.g., has the user cut back on spending), user input 820 by the user, and/or other goal progress information over measurement feedback channels. In an example, parameters and/or statistical analysis performed by the model may be modified based upon whether the goal progress information indicates that the user did or did not make progress towards the financial goal 808 after viewing the vacation documentary 804.

Figure 9:
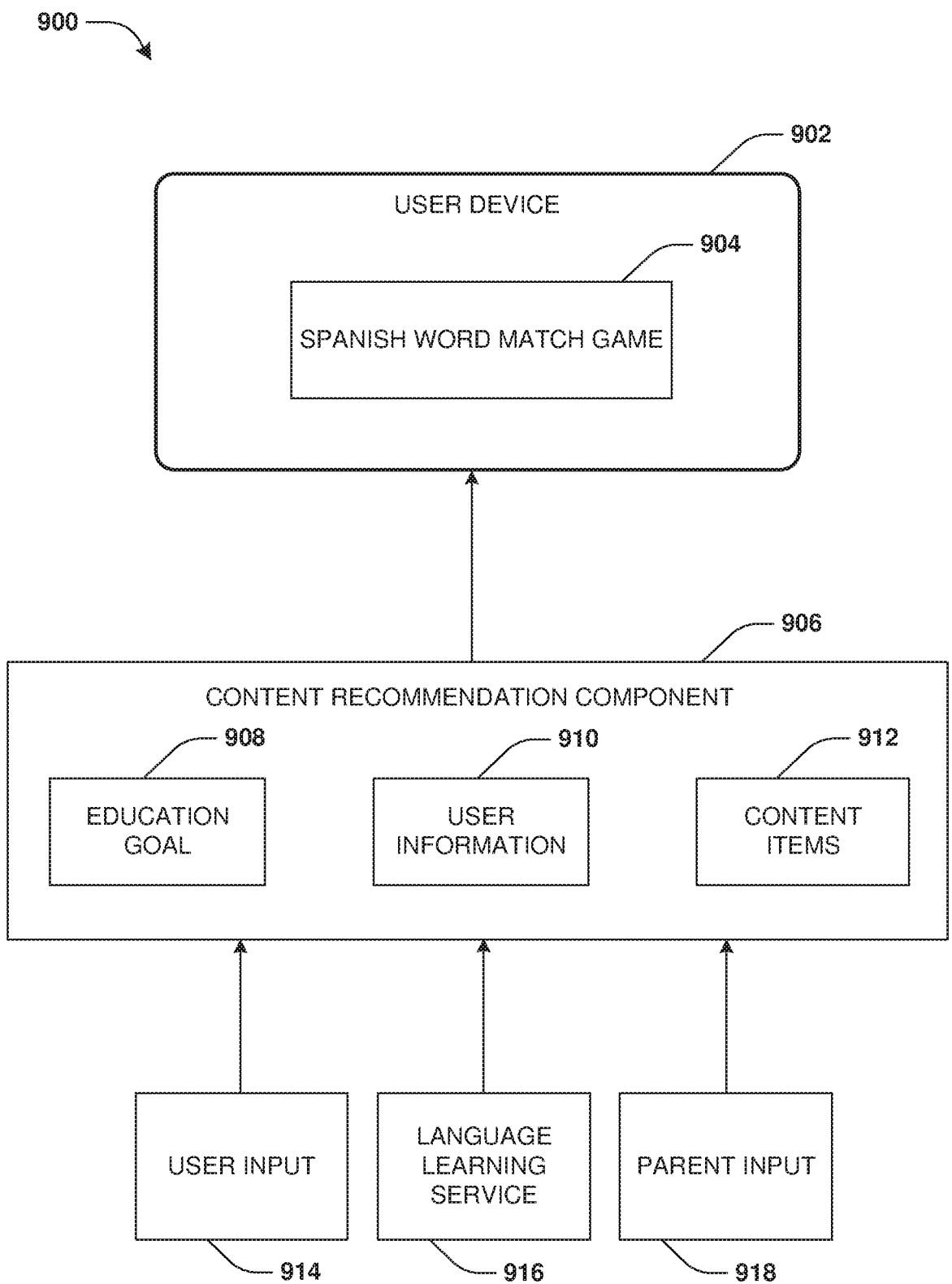
FIG. 9 is a component block diagram illustrating an example system for content item selection for goal achievement, where a model is utilized to select a content item to provide to a user having an education goal.

FIG. 9 illustrates a system 900 for content item selection for goal achievement. A user may utilize a user device 902 (e.g., a mobile phone, a smart device, a laptop, a videogame console, a smart television, etc.) to access a media channel registered with a content recommendation component 906. For example, the user may utilize the user device 902, such as a videogame console, tablet, or other device, to access a videogame service. The content recommendation component 906 may receive a notification that the user is accessing the videogame service. In an embodiment, the user may have previously register with the content recommendation component 906. The user (or a parent) may have provided the content recommendation component 906 with an indication that the user is trying to learn Spanish as an education goal 908. The user (or the parent) may have provided the content recommendation component 906 with user information 910, such as an age, a gender, access information to a learning language service that the parent of the user purchased for the user, school information, parent information, and/or a variety of other information.

The content recommendation component 906 may utilize a model (e.g., model 616 of FIG. 6) to evaluate the educational goal 908 of learning Spanish, the user information 910, and a set of content items 912 (e.g., images, videos, links to websites, recommendations, text, etc.) to generate predictions for the content items of how likely each content item will be a causation factor of the user making progress towards the education goal 908 in response to the user being provided with each content item. For example, the model may output an increase in probability that the user will make progress towards the education goal 908 if provided with a Spanish word matching game 904 to play than a probability that the user makes progress towards the education goal 908 without being provided with the Spanish word matching game 904. The increase in probability may relate to how strong of a causation factor the Spanish word matching game 904 is towards inspiring/motivating the user to make progress towards the education goal 908, which may be utilized as a ranking factor. In response to the Spanish word matching game 904 having a predicted likelihood of being the causation factor above a threshold (e.g., a larger predicted likelihood/ranking factor than other content items), the content recommendation component 906 displays the Spanish word matching game 904 through the videogame service.

Progress of the user towards the education goal 908 in response to being provided with the Spanish word matching game 904 may be tracked as feedback for further training the model and/or for subsequently selecting content items to provide to the user. For example, the content recommendation component 906 may obtain user input 914, course progress by the user with the language learning service 916, parent input 918, and/or other goal progress information over measurement feedback channels. In an example, parameters and/or statistical analysis performed by the model may be modified based upon whether the goal progress information indicates that the user did or did not make progress towards the education goal 908 after playing the Spanish word matching game 904.

Figure 10:
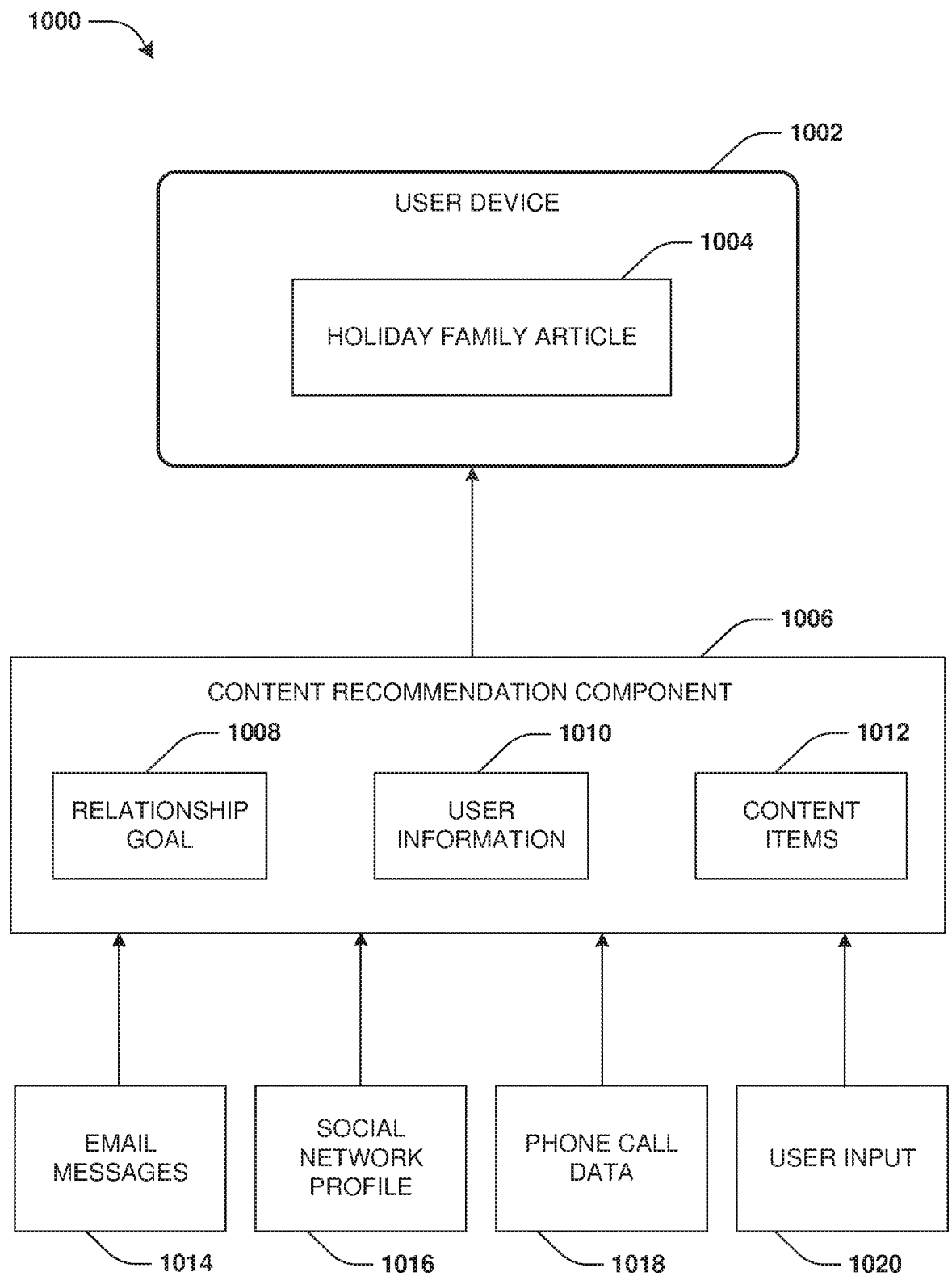
FIG. 10 is a component block diagram illustrating an example system for content item selection for goal achievement, where a model is utilized to select a content item to provide to a user having a relationship goal.

FIG. 10 illustrates a system 1000 for content item selection for goal achievement. A user may utilize a user device 1002 (e.g., a mobile phone, a smart device, a laptop, a videogame console, a smart television, etc.) to access a media channel registered with a content recommendation component 1006. For example, the user may utilize the user device 1002 to access a news website. The content recommendation component 1006 may receive a notification that the user is accessing the news website. In an embodiment, the user may have previously register with the content recommendation component 1006. The user may have provided the content recommendation component 1006 with an indication that the user is trying to keep in better contact with a cousin as a relationship goal 1008. The user may have provided the content recommendation component 1006 with user information 1010, such as an age, a gender, family member information, location information, how to access email messages 1014 of the user, how to access a social network profile 1016 of the user, how to access phone call and message data 1018 of the user, and/or a variety of other information.

The content recommendation component 1006 may utilize a model (e.g., model 616 of FIG. 6) to evaluate the relationship goal 1008 of keeping in better contact with the cousin, the user information 1010, and a set of content items 1012 (e.g., images, videos, links to websites, recommendations, text, etc.) to generate predictions for the content items of how likely each content item will be a causation factor of the user making progress towards the relationship goal 1008 in response to the user being provided with each content item. For example, the model may output an increase in probability that the user will make progress towards the relationship goal 1008 if provided with a holiday family article 1004 to read than a probability that the user makes progress towards the relationship goal 1008 without being provided with the holiday family article 1004. The increase in probability may relate to how strong of a causation factor the holiday family article 1004 is towards inspiring/motivating the user to make progress towards the relationship goal 1008, which may be utilized as a ranking factor. In response to the holiday family article 1004 having a predicted likelihood of being the causation factor above a threshold (e.g., a larger predicted likelihood/ranking factor than other content items), the content recommendation component 1006 displays the holiday family article 1004 through the news website.

Progress of the user towards the relationship goal 1008 in response to being provided with the holiday family article 1004 may be tracked as feedback for further training the model and/or for subsequently selecting content items to provide to the user. For example, the content recommendation component 1006 may obtain the email messages 1014 (e.g., did the user email the cousin and at what frequency), the social network profile 1016 (e.g., did the user message or interact with the cousin through a social network), the phone call and message data 1018 (e.g., did the user call or message the cousin and at what frequency), user input 1020, and/or other goal progress information over measurement feedback channels. In an example, parameters and/or statistical analysis performed by the model may be modified based upon whether the goal progress information indicates that the user did or did not make progress towards the relationship goal 1008 after reading the holiday family article 1004.

Figure 11:
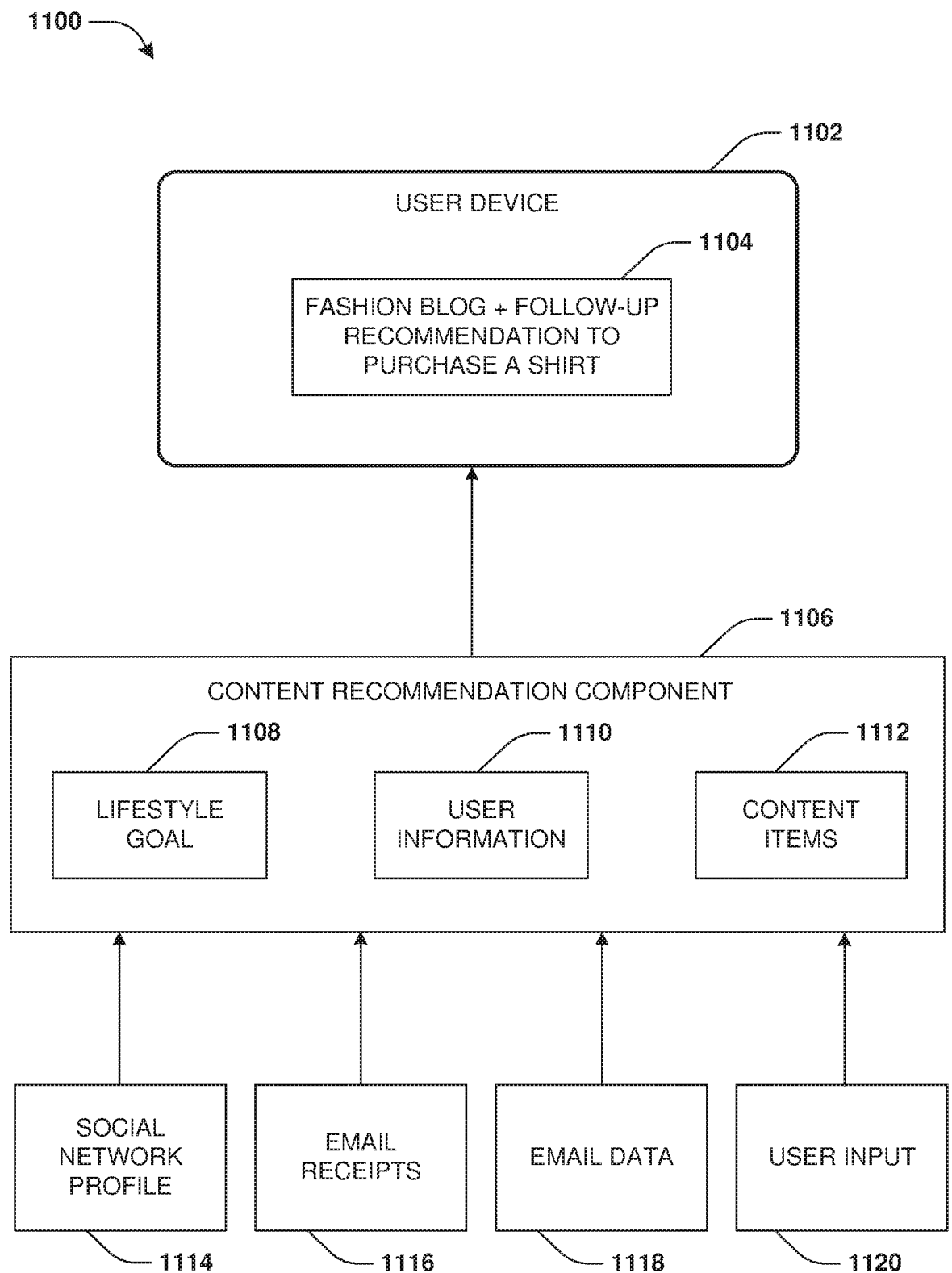
FIG. 11 is a component block diagram illustrating an example system for content item selection for goal achievement, where a model is utilized to select a content item to provide to a user having a lifestyle goal.

FIG. 11 illustrates a system 1100 for content item selection for goal achievement. A user may utilize a user device 1102 (e.g., a mobile phone, a smart device, a laptop, a videogame console, a smart television, etc.) to access a media channel registered with a content recommendation component 1106. For example, the user may utilize the user device 1102 to access a blogging service. The content recommendation component 1106 may receive a notification that the user is accessing the blogging service. In an embodiment, the user may have previously register with the content recommendation component 1106. The user may have provided the content recommendation component 1106 with an indication that the user is trying to keep up with current fashion trends as a lifestyle goal 1108. The user may have provided the content recommendation component 1106 with user information 1110, such as an age, a gender, clothing size, shoe size, location information, how to access a social network profile 1114 of the user, how to access receipts 1116 of the user, how to access email data 1118 of the user, and/or a variety of other information.

The content recommendation component 1106 may utilize a model (e.g., model 616 of FIG. 6) to evaluate the lifestyle goal 1108 of keeping up with current fashion trends, the user information 1110, and a set of content items 1112 (e.g., images, videos, links to websites, recommendations, text, etc.) to generate predictions for the content items of how likely each content item will be a causation factor of the user making progress towards the lifestyle goal 1108 in response to the user being provided with each content item. For example, the model may output an increase in probability that the user will make progress towards the lifestyle goal 1108 if provided with a fashion blog 1104 to read than a probability that the user makes progress towards the lifestyle goal 1108 without being provided with the fashion blog 1104. The increase in probability may relate to how strong of a causation factor the fashion blog 1104 is towards inspiring/motivating the user to make progress towards the lifestyle goal 1108, which may be utilized as a ranking factor. In response to the fashion blog 1104 having a predicted likelihood of being the causation factor above a threshold (e.g., a larger predicted likelihood/ranking factor than other content items), the content recommendation component 1106 displays the fashion blog 1104 through the blogging service.

Progress of the user towards the lifestyle goal 1108 in response to being provided with the fashion blog 1104 may be tracked as feedback for further training the model and/or for subsequently selecting content items to provide to the user. For example, the content recommendation component 1106 may obtain social network data from the social network profile 1114, the receipts 1116, the email data 1118, user input 1120, and/or other goal progress information over measurement feedback channels (e.g., information as to whether the user is purchasing certain types of clothing, whether the user is reading fashion blogs, whether the user is engaging in social media conversations about fashion, etc.). In an example, parameters and/or statistical analysis performed by the model may be modified based upon whether the goal progress information indicates that the user did or did not make progress towards the lifestyle goal 1108 after reading the fashion blog 1104. An activity related to the fashion blog 1104 and/or the lifestyle goal 1108 may be identified and subsequently provided to the user, such as a follow-up recommendation to purchase a shirt.

Figure 12:
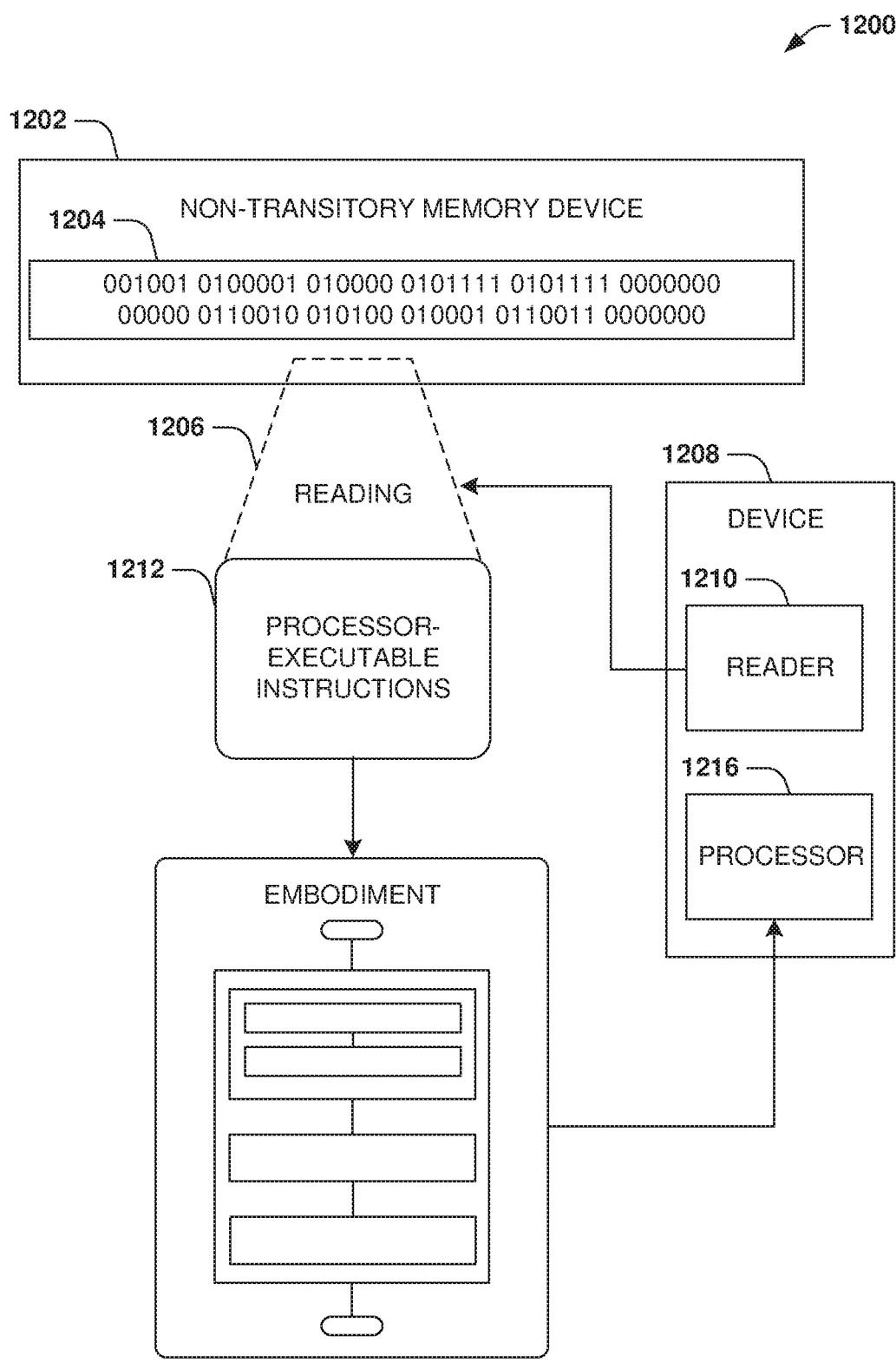
FIG. 12 is an illustration of a scenario featuring an example non-transitory machine readable medium in accordance with one or more of the provisions set forth herein.

FIG. 12 is an illustration of a scenario 1200 involving an example non-transitory machine readable medium 1202. The non-transitory machine readable medium 1202 may comprise processor-executable instructions 1212 that when executed by a processor 1216 cause performance (e.g., by the processor 1216) of at least some of the provisions herein. The non-transitory machine readable medium 1202 may comprise a memory semiconductor (e.g., a semiconductor utilizing static random access memory (SRAM), dynamic random access memory (DRAM), and/or synchronous dynamic random access memory (SDRAM) technologies), a platter of a hard disk drive, a flash memory device, or a magnetic or optical disc (such as a compact disk (CD), a digital versatile disk (DVD), or floppy disk). The example non-transitory machine readable medium 1202 stores computer-readable data 1204 that, when subjected to reading 1206 by a reader 1210 of a device 1208 (e.g., a read head of a hard disk drive, or a read operation invoked on a solid-state storage device), express the processor-executable instructions 1212. In some embodiments, the processor-executable instructions 1212, when executed cause performance of operations, such as at least some of the example method 400 of FIG. 4, for example. In some embodiments, the processor-executable instructions 1212 are configured to cause implementation of a system, such as at least some of the example system 500 of FIG. 5, at least some of the example system 600 of FIG. 6, at least some of the example system 700 of FIG. 7, at least some of the example system 800 of FIG. 8, at least some of the example system 900 of FIG. 9, at least some of the example system 1000 of FIG. 10, and/or at least some of the example system 1100 of FIG. 11, for example.

3. Usage of Terms

As used in this application, "component," "module," "system", "interface", and/or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Unless specified otherwise, "first," "second," and/or the like are not intended to imply a temporal aspect, a spatial aspect, an ordering, etc. Rather, such terms are merely used as identifiers, names, etc. for features, elements, items, etc. For example, a first object and a second object generally correspond to object A and object B or two different or two identical objects or the same object.

Moreover, "example" is used herein to mean serving as an example, instance, illustration, etc., and not necessarily as advantageous. As used herein, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", and/or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Various operations of embodiments are provided herein. In an embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein. Also, it will be understood that not all operations are necessary in some embodiments.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A method, comprising:
   executing, on a processor of a computing device, instructions that cause the computing device to perform operations, the operations comprising:
   identifying a goal of a user;
   utilizing a machine learning model to evaluate the goal, user information, and a set of content items to generate predictions for the content items of how likely each content item will be a causation factor of the user making progress towards the goal in response to the user being provided with each content item, wherein the predictions for the content items comprise (i) a first predicted likelihood that viewing a first content item will cause the user to make progress towards the goal and (ii) a second predicted likelihood that viewing a second content item will cause the user to make progress towards the goal,
   the machine learning model trained based upon data indicative of one or more activities of at least one of the user or one or more other users;
   selecting a target content item, based upon the predictions generated utilizing the machine learning model, from the set of content items based upon the target content item having a predicted likelihood of being the causation factor above a threshold;
   providing, via a network connection, the target content item through a registered media channel accessible through a device of the user;
   tracking, via one or more network connections, feedback comprising data indicative of one or more further activities indicative of progress of the user towards the goal after providing the target content item to the user;
   training the machine learning model, based upon the tracked feedback comprising the data indicative of the one or more further activities indicative of progress, to generate a trained machine learning model;
   utilizing the trained machine learning model to generate second predictions; and
   providing one or more content items based upon the second predictions generated utilizing the trained machine learning model.

2. The method of claim 1, comprising:
   statistically filtering the set of content items to identify content items that correlate to goal progress for groups of users.

3. The method of claim 1, comprising:
   performing A/B testing for a content item by tracking whether a first set of users provided with the content item made progress towards the goal and whether a second set of users not provided with the content item made progress towards the goal.

4. The method of claim 1, wherein the machine learning-model comprises a function with an input of an item input, a user input, and a goal input, and wherein the function outputs an increase in probability that the user will make progress towards the goal if provided with the content item based upon a difference between a probability the user makes progress towards the goal if provided with the content item and a probability the user makes progress towards the goal if the user is not provided with the content item.

5. The method of claim 1, wherein the machine learning-model maps a combination of user, item, and goal to a difference in probability that a target user will make progress towards a target goal if a content item is provided to the target user.

6. The method of claim 1, comprising:
   tracking progress of users towards goals based upon content items provided to the users.

7. The method of claim 6, comprising:
   generating historical data for each user relating to content items provided to each user and goal progress data.

8. The method of claim 7, comprising:
   clustering similar users into clusters;
   identifying a cluster to which the user belongs; and
   utilizing an aggregate of historical data of users within the cluster as an input to the machine learning model for selecting the target content item for the user.

9. The method of claim 1, wherein the target content item comprises a recommendation to take a break from content consumption.

10. The method of claim 1, comprising:
    identifying a set of goals of the user; and
    applying weights of relative importance for each goal within the set of goals.

11. The method of claim 10, comprising:
    utilizing a weighted average of increases in successive probabilities of the user making progress over each goal to rank content items.

12. A non-transitory machine readable medium having stored thereon processor-executable instructions that when executed cause performance of operations, the operations comprising:
    utilizing a machine learning model to evaluate a goal of a user, user information, and a set of content items to generate predictions for the content items of how likely each content item will be a causation factor of the user making progress towards the goal in response to the user being provided with each content item, wherein the predictions for the content items comprise (i) a first predicted likelihood that viewing a first content item will cause the user to make progress towards the goal and (ii) a second predicted likelihood that viewing a second content item will cause the user to make progress towards the goal,
    the machine learning model trained based upon data indicative of one or more activities of at least one of the user or one or more other users;
    selecting a target content item, based upon the predictions generated utilizing the machine learning model, from the set of content items based upon the target content item having a predicted likelihood of being the causation factor above a threshold;
    providing, via a network connection, the target content item to the user;
    tracking, via one or more network connections, feedback comprising data indicative of one or more further activities indicative of progress of the user towards the goal after providing the target content item to the user; and
    training the machine learning model, based upon the tracked feedback comprising the data indicative of the one or more further activities indicative of progress, to generate a trained machine learning model.

13. The non-transitory machine readable medium of claim 12, wherein the tracking is performed through a goal measurement feedback channel corresponding to at least one of user input, output of device equipment, or input from a third party.

14. The non-transitory machine readable medium of claim 12, wherein the user achieving the goal is an objective of the machine learning-model, and wherein the operations comprise:
utilizing output from a system, with a target objective different than the objective of the machine learning model, to rank the set of content items.

15. The non-transitory machine readable medium of claim 12, wherein the operations comprise:
maintaining a user repository of age data, gender data, home location data, work location data, and media preference data of users;
maintaining a media repository of metadata about content items and relationships between content items corresponding to overlap of at least one of authorship data, theme data, location data, actors data, users experiencing content items, and time of users experiencing content items; and
applying the machine learning model to data within the user repository and the media repository for selecting the target content item.

16. A computing device comprising:
a processor; and
memory comprising processor-executable instructions that when executed by the processor cause performance of operations, the operations comprising:
utilizing a machine learning model to evaluate a goal of a user, user information, and a set of content items to generate predictions for the content items of how likely each content item will be a causation factor of the user making progress towards the goal in response to the user being provided with each content item, wherein the predictions for the content items comprise (i) a first predicted likelihood that viewing a first content item will cause the user to make progress towards the goal and (ii) a second predicted likelihood that viewing a second content item will cause the user to make progress towards the goal,
selecting a target content item, based upon the predictions generated utilizing the machine learning model, from the set of content items based upon the target content item having a predicted likelihood of being the causation factor above a threshold;
providing, via a network connection, the target content item to the user;
tracking, via one or more network connections, feedback comprising data indicative of one or more further activities indicative of progress of the user towards the goal after providing the target content item to the user; and
training the machine learning model, based upon the tracked feedback comprising the data indicative of the one or more further activities indicative of progress, to generate a trained machine learning model.

17. The computing device of claim 16, wherein the tracking is performed through a goal measurement feedback channel corresponding to at least one of user input, output of device equipment, or input from a third party.

18. The computing device of claim 16, wherein the user achieving the goal is an objective of the machine learning model, and wherein the operations comprise:
utilizing output from a system, with a target objective different than the objective of the machine learning model, to rank the set of content items.

19. The computing device of claim 16, wherein the operations comprise:
maintaining a user repository comprising at least one of age data, gender data, home location data, work location data, or media preference data of users; and
applying the machine learning model to data within the user repository for selecting the target content item.

20. The computing device of claim 16, wherein the operations comprise:
maintaining a media repository of metadata about content items and relationships between content items corresponding to overlap of at least one of authorship data, theme data, location data, actors data, users experiencing content items, or time of users experiencing content items; and
applying the machine learning model to data within the media repository for selecting the target content item.

* * * * *